(12) United States Patent
Douglas et al.

(10) Patent No.: US 10,773,123 B1
(45) Date of Patent: Sep. 15, 2020

(54) SYSTEMS AND METHODS FOR WEARABLE DEVICES THAT DETERMINE BALANCE INDICES

(71) Applicant: BioMech Sensor LLC, Midlothian, VA (US)

(72) Inventors: John Douglas, Potomac, MD (US); Frank Fornari, Naples, FL (US)

(73) Assignee: BioMech Sensor LLC, Midlothian, VA (US)

( * ) Notice: Subject to any disclaimer, the term of this patent is extended or adjusted under 35 U.S.C. 154(b) by 0 days.

(21) Appl. No.: 16/558,019

(22) Filed: Aug. 30, 2019

(51) Int. Cl.
*A63B 24/00* (2006.01)

(52) U.S. Cl.
CPC ...... *A63B 24/0006* (2013.01); *A63B 24/0021* (2013.01); *A63B 24/0075* (2013.01); *A63B 2024/0071* (2013.01); *A63B 2220/34* (2013.01); *A63B 2220/836* (2013.01)

(58) Field of Classification Search
CPC .................. A63B 2220/34; A63B 2220/83
See application file for complete search history.

(56) References Cited

U.S. PATENT DOCUMENTS

| | | | | |
|---|---|---|---|---|
| 7,857,708 B2* | 12/2010 | Ueda | .................. | A63B 24/0003 382/103 |
| 2008/0281550 A1* | 11/2008 | Hogle | .................. | A61B 5/1038 702/127 |
| 2010/0323805 A1* | 12/2010 | Kamino | ............. | A63B 24/0006 473/221 |
| 2011/0230986 A1* | 9/2011 | Lafortune | ............ | A43B 3/0005 700/93 |
| 2014/0156040 A1* | 6/2014 | Mooney | ................. | A63B 69/36 700/91 |
| 2016/0236034 A1* | 8/2016 | Sato | .................... | A63B 69/3632 |
| 2019/0347956 A1* | 11/2019 | Daga | .................. | G09B 19/0038 |

* cited by examiner

*Primary Examiner* — Mohamed Charioui

(74) *Attorney, Agent, or Firm* — Finnegan, Henderson, Farabow, Garrett & Dunner LLP

(57) ABSTRACT

A wearable device for determining balance of a user is provided, comprising a gyroscope, an inertial measurement device, a memory storing instructions, and a processor configured to execute the instructions to perform operations, comprising receiving angular velocity measurements over a period of time from the gyroscope, receiving deviations from the second axis over the period of time from the inertial measurement device, weighting the deviations from the second axis based on directions associated with the deviations, receiving deviations from the third axis over the period of time from the inertial measurement device, weighting the deviations from the third axis based on directions associated with the deviations, and based on the angular velocity measurements, the weighted deviations from the second axis, and the weighted deviations from the third axis, determining an index associated with a left side of the user and an index associated with a right side of the user.

20 Claims, 14 Drawing Sheets

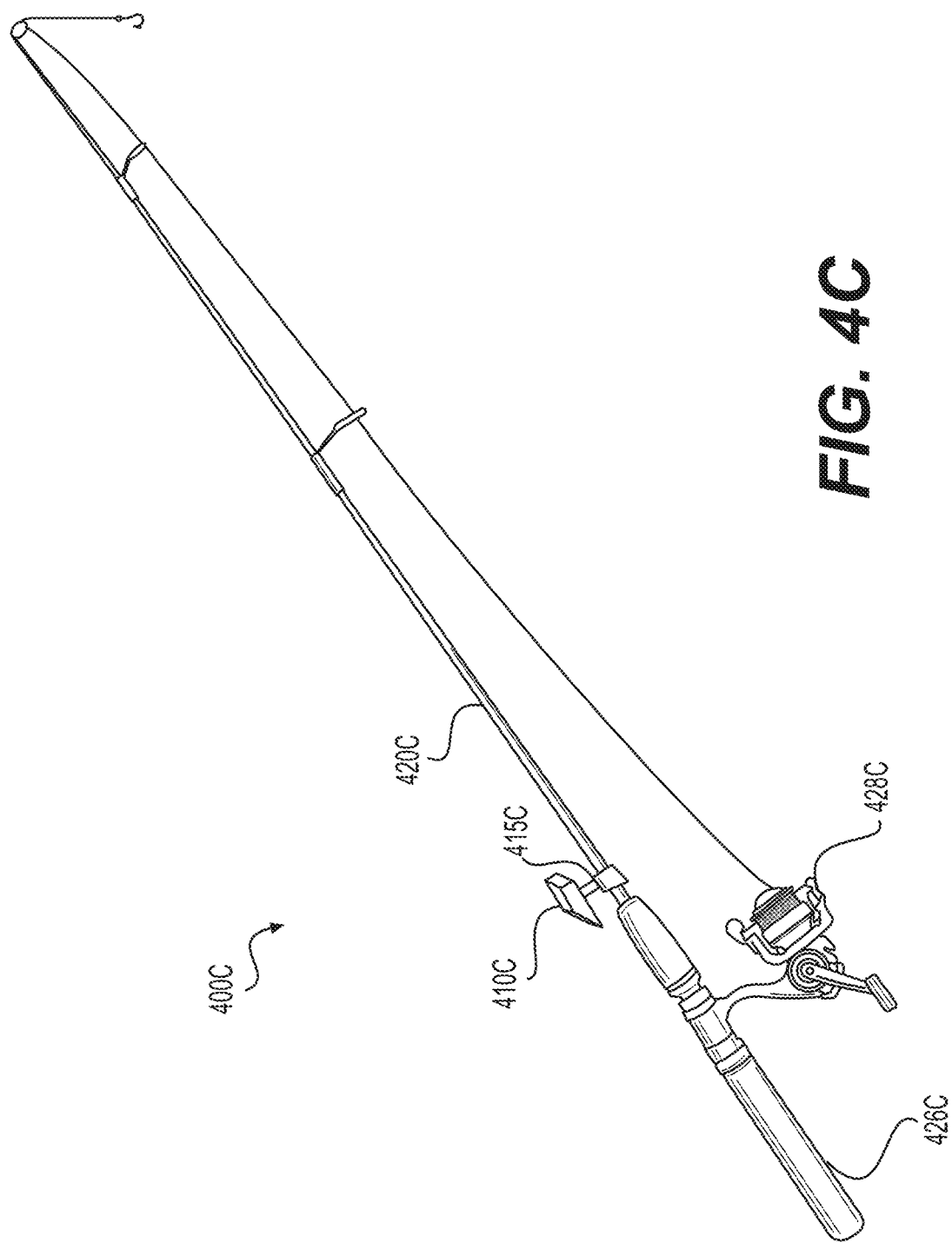

US 10,773,123 B1

SYSTEMS AND METHODS FOR WEARABLE DEVICES THAT DETERMINE BALANCE INDICES

TECHNICAL FIELD

This disclosure relates generally to wearable devices, and more particularly to methods and systems for measure balance using wearable devices.

BACKGROUND

Wearable devices continue to increase in popularity. For example, wrist-worn fitness trackers record and display a user's steps taken over the course of a day. Other devices record accelerometer measurements and alert a medical professional to a possible fall event for older patients.

However, wearable devices usually include a single gyroscope or inertial measurement unit (IMU). Accordingly, measurements usually suffer from low accuracy and drift. Some solutions include the use of expensive and large laboratories that use more accurate visual analysis to avoid errors inherent in wearable components. However, such solutions are impractical for most uses and cannot scale.

Moreover, many existing calculations regarding balance (e.g., deviations from plumb) are rough and fail to account for how human reflexes function. In particular, minor yet rapid deviations from plumb are over-weighed in extant models even through such reflexes represent normal balancing techniques.

SUMMARY

Disclosed embodiments may include methods, systems, and computer-readable media to calculate balance measures using wearable components. Accordingly, embodiments of the present disclosure provide technical solutions to the technical problems with conventional apparatuses, e.g., by correcting for drift and other error, and technical problems with conventional models, e.g., by more accurately modeling human balancing reflexes. For example, embodiments of the present disclosure may result in a more accurate balancing measure while retaining the efficiency and cost-effectiveness of wearable components.

In one embodiment, a wearable device for determining balance of a user may comprise at least one gyroscope configured to measure angular velocity about a first axis; at least one inertial measurement device configured to measure deviation along a second axis and a third axis; at least one memory storing instructions; and at least one processor configured to execute the instructions to perform operations. the operations may comprise receiving angular velocity measurements over a period of time from the at least one gyroscope; receiving deviations from the second axis over the period of time from the at least one inertial measurement device; weighting the deviations from the second axis based on directions associated with the deviations; receiving deviations from the third axis over the period of time from the at least one inertial measurement device; weighting the deviations from the third axis based on directions associated with the deviations; and generating a composite balance index based on the angular velocity measurements, the weighted deviations from the second axis, and the weighted deviations from the third axis.

In one embodiment, a wearable device for determining balance of a user may comprise at least one gyroscope configured to measure angular velocity about a first axis; at least one inertial measurement device configured to measure deviation along a second axis and a third axis; at least one memory storing instructions; and at least one processor configured to execute the instructions to perform operations. The operations may comprise receiving angular velocity measurements over a period of time from the at least one gyroscope; receiving deviations from the second axis over the period of time from the at least one inertial measurement device; weighting the deviations from the second axis based on directions associated with the deviations; receiving deviations from the third axis over the period of time from the at least one inertial measurement device; weighting the deviations from the third axis based on directions associated with the deviations; and based on the angular velocity measurements, the weighted deviations from the second axis, and the weighted deviations from the third axis, determining an index associated with a left side of the user and an index associated with a right side of the user.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIGS. 4A, 4B, 4C, and 4D illustrate different equipment with a sensor device in accordance with some embodiments of the present disclosure.

DETAILED DESCRIPTION

Figure 1:
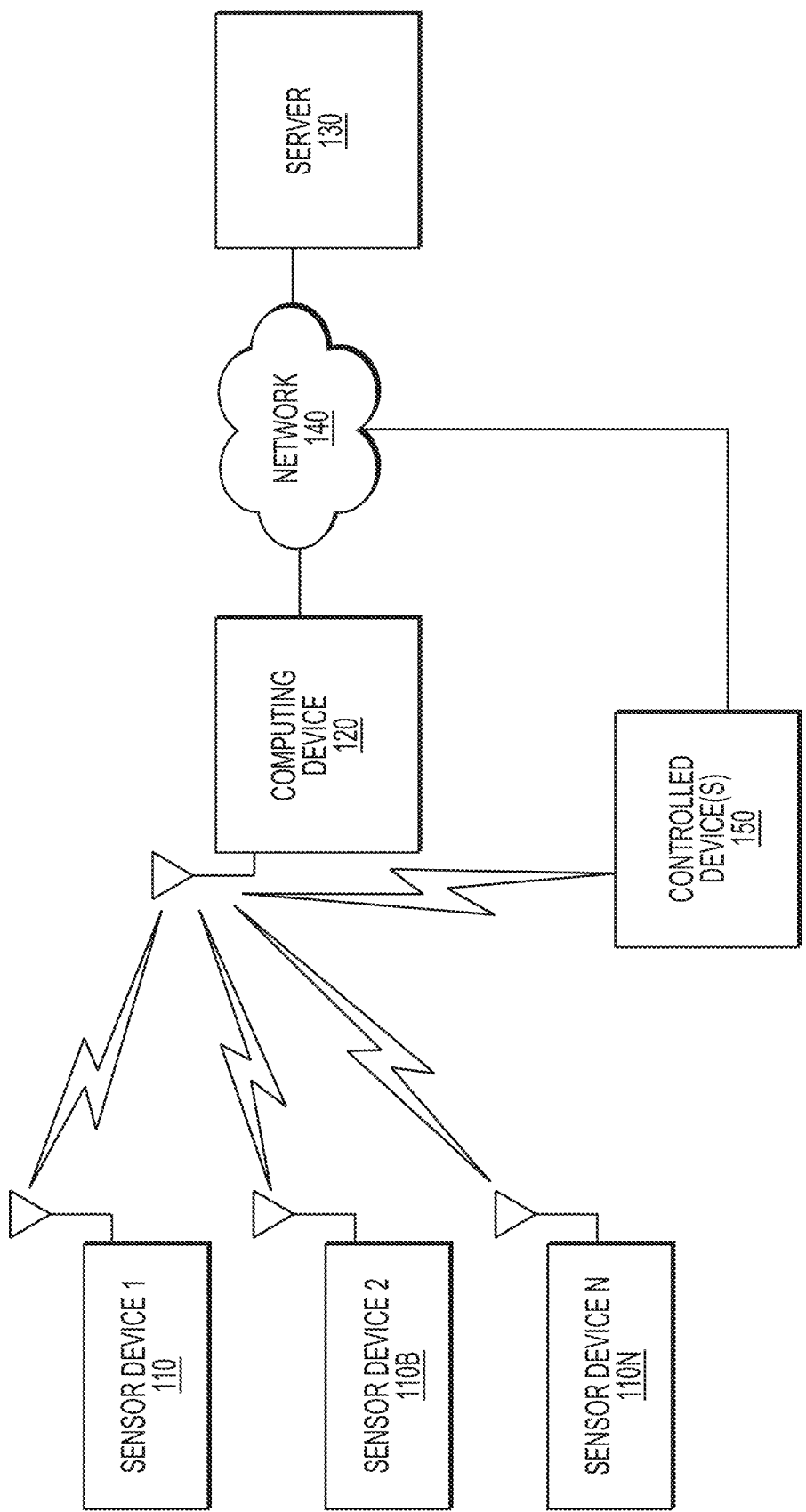
FIG. 1 illustrates an exemplary real-time data acquisition, analysis, and feedback system according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Disclosed embodiments generally relate to systems and methods of acquiring data in real-time, analyzing the data, and providing real-time feedback to the user. Disclosed embodiments may track, quantify, and evaluate body motion of a user and/or equipment or machinery. For example, while moving or exercising, disclosed systems and methods may process sensor data quantifying clinically relevant characteristics of a running stride of a user, as well as evaluate the data by comparing it to simultaneously received data from another user, prior sets of data from the user or other users, and/or model (also referred to as "template") sets of data for a desired running stride. In this example, a user may receive feedback mid-stride or mid-repetition that the movement or action fails to conform to the template set of data. For a single motion or exercise session or for discrete motions performed throughout a session, disclosed systems may provide a quantified measurement of the motion, such as a normalized "score" or percentage deviation between the test and template data sets. For example, particular embodiments may calculate a composite balance score, a left balance score, and/or a right balance score for a user. Further, over time, disclosed systems may automatically adapt templates based on progress from prior measurements and long-term goals, making sure captured data from a user's motion or motions matches desired criteria, such as orientation, speed, and/or range of motion, for example. Over time, disclosed systems may allow for cloud-based review of progress by the user or a third party (e.g., a healthcare professional), highlighting problematic results that may benefit from specialized treatment, which may include modifications to exercises or instructive motions, different motion instructions altogether, a varied combination of regimens, medication, and/or surgical treatment. Additionally or alternatively, problematic balance scores may indicate fall risks for clinicians, poor stride for equestrian competitors, or other problems requiring supervision and/or intervention.

Existing systems and methods may only track a single metric over time. Disclosed embodiments may offer the improved functionality of accounting for and correlating different variables associated with an activity. Disclosed embodiments may offer an improved solution by correlating different tracked data over time and recognizing relevant trends or patterns in the data that may not be apparent without multidimensional correlation. Moreover, disclosed embodiments may use multidimensional data to resolve problems with single variables (e.g., drift from gyroscopes and magnetometers, jitter from accelerometers, or the like) and to weigh measurements in different dimensions differently to produce more realistic analyses.

Existing systems further lack the capability to provide real-time feedback. Disclosed embodiments may offer an improved solution by providing an automatic, immediate, and clinically relevant indication to a user that acquired data fails to match desired characteristics, as well as receiving manual feedback and providing it to the user in real-time. For example, disclosed embodiments may provide real-time feedback to users based on pattern matching algorithms. When received sensor data matches a predefined rule, the sensor or an associated device may provide an indication to the user (e.g., visually, audibly, and/or tangibly). In other examples, real-time data is provided to a third party (e.g., a coach, trainer, doctor, healthcare professional), offering the third party the option to input feedback that systems then transmit to a user in real-time. The relevant real-time feedback, automatic and/or manual, may allow the user to adapt mid-activity, allowing for users to more effectively practice physical movements, for example.

Further, existing systems fail to track changes over time. Disclosed embodiments may offer the improvement of highlighting clinically relevant trends over time between different data profiles. Further, disclosed embodiments may track clinically relevant progress, such as a range of motion or deviation from a template profile. For example, systems and methods may determine that a deviation in a user's walking stride has digressed (e.g., a limp in a user's walk) at a particular magnitude or duration that may present a significant health risk or long-term problem. In another example, systems and methods may determine that a deviation in a user's balance (e.g., indicated in a composite score, a left score, a right score, or the like) has digressed and may present a fall risk, a lack of progress in physical therapy, or the like. While such examples may be apparent to the user, exemplary disclosed systems may also uncover latent changes in a user's wellbeing, such as changes in blood-glucose levels, blood pressure, heart rate, oxidation levels, and hydration, for example. Embodiments may correlate such clinically relevant latent characteristics of a user's body with other activities to note trends of problematic activity. Systems and methods may alert the user and/or a healthcare provider. Moreover, insurance providers may use disclosed systems and methods to offer adapted insurance options tailored to an individual, such as decreasing one's rates for maintaining a lower blood pressure through proper medication, diet, and exercise, or advocating for surgical intervention prior to complete failure of some physiological aspect that would otherwise hamper recovery.

Disclosed embodiments may improve on existing systems by adapting goals, such as to reach a desired outcome and/or based on current results. For example, a user's progress may increase or decrease based on environmental factors and the user's unique physiology. When user performance exceeds planned or expected progress, disclosed embodiments may adapt templates to be more aggressive (e.g., higher range of motion, faster, stronger, longer distances, more repetitions, tighter tolerances to a template). However, if a user's progress stagnates or declines, disclosed embodiments may allow for a more relaxed adaptation of a user's template.

Disclosed embodiments may provide one or more of these improvements. Additional improvements may be present in the embodiments but not explicitly listed here. Further, embodiments need not meet one or more of these outlined benefits to necessarily provide advancement over current technology. Additional advancements are discussed throughout this disclosure.

Disclosed embodiments may include generating, utilizing, and/or manipulating a data profile. In some embodiments, a data profile may be a multidimensional data stream over time or a portfolio of multiple time-synchronized streams of data. A data profile may correlate two or more time-dependent sets of data, such as data received from various sensors. For example, a data profile may represent acceleration in three axes over time. In another example, a data profile may include an accumulated magnitude of movement (e.g., an activity measurement metric) and a recorded blood glucose level over time, or a heartrate, blood pressure, muscle operation, and an activity measurement metric over time. In still further examples, data from electromyography (EMG) sensors, temperature sensors, elevation sensors, light intensity sensors, pressure sensors, force sensors, and electrical sensors may be correlated with health information, such as blood-glucose levels, heartrate, blood pressure, oxygen saturation levels, body temperature, respiratory rate, and/or gait. Other types of data streams may be generated using the sensors and types of data discussed in this specification, consistent with disclosed embodiments. Correlations of performance or health related to elevation, light intensity, temperature, humidity or other external factors are expected.

Disclosed embodiments may include generating, utilizing, and/or manipulating a motion profile. A motion profile may be a data profile that describes the motion of an object, person, and/or extremity over time. A motion profile may include a timewise multidimensional record of motion. For example, motion profiles may include three-dimensional acceleration data, three-axis orientation data, three-axis angular velocity data, and/or three-axis gravitational information over time. In some embodiments, the acceleration and/or orientation data may include data for less than three dimensions, such as single or dual axis acceleration and/or orientation data. The motion profile may combine unique signals of the same motion, such as correlating linear acceleration and angular acceleration.

Based on the motion profile, disclosed embodiments may include rendering a graphical representation of a corresponding motion in space. In the example of a three-dimensional motion profile, disclosed embodiments may include rendering a line in a three-axis space illustrating the path of the object. In still further embodiments, the rendered display may include an animation showing an icon oriented (e.g., based on orientation data) and moving along the path at a rate commensurate with the acceleration data of the motion profile. Such data may also be rendered alongside or overlaid on top of synchronized captured video data.

Additionally with or alternatively to the graphical representation, disclosed embodiments may include calculating a balance score based on a user's corresponding motion. As described in greater detail below, disclosed embodiments may calculate a balance score using changes in angular velocity weighted by direction rather than solely deviations from plumb.

Disclosed embodiments may include comparing two or more motion profiles or, more generally, data profiles. In some embodiments, systems and methods may determine the magnitude of the differences between two profiles. Such differences may indicate how closely two sets of data match, such as two swings of a golf club. The differences may be quantified using different calculations. In one example, disclosed embodiments may sum the aggregate difference of a fixed period of time (e.g., integrate the differences). Some embodiments may normalize the integrated amount on a per unit time basis. Additionally or alternatively, disclosed embodiments may include comparing two profiles by determining that at a predefined set of points in time (e.g., one or more timewise data points) the two profiles differed by more than a threshold amount (e.g., a predefined threshold or an automatically adjusted threshold). Additionally or alternatively, disclosed embodiments may include comparing balance scores, e.g., using subtraction or any other weighted comparison.

Disclosed embodiments may include utilizing event models to recognize data profiles, motion profiles, or portions of either that match particular criteria. These criteria may include simple thresholds or complex curve-matching algorithms. In the example of complex curve fitting, an event model may be defined by a specified contour for particular variables of a profile, such that the y-axis displacement (e.g., ordinary least squares difference) or orthogonal distance (e.g., total least squares difference) is below a threshold amount. The amount may be normalized based on the type of application or magnitude of the test profile data.

Disclosed embodiments may use one or more of these concepts individually or in combination as discussed below regarding the figures.

FIG. 1 illustrates an exemplary real-time data quantification, acquisition, analysis, and feedback system 100 according to some embodiments of the present disclosure. System 100 may include one or more sensor devices (110, 110B, 110N), computing device 120, controlled device(s) 150, network 140, and server 130.

System 100 may include one or more sensor devices to aggregate sensor data. Sensor devices 110, 110B, and 110N represent the one or more sensor devices that provide data to system 100. Each of the shown sensor devices may include the same sensor capabilities or different capabilities. For example, sensor device 110 may include an inertial measurement unit, while sensor device 110B provides pressure data (e.g., from the grip of a club or racket, or from an insole). In a differing example, the entire sensor shown could only include inertial measurement units, but could be located on different people, or on different points of a single person (e.g., wrist, knee, or ankle). Sensors may provide various sensed data to system 100 as further discussed below.

System 100 may include computing device 120. In some embodiments, computing device 120 may be a general purpose computer, tablet device, smartphone, or smart watch. Computing device 120 may include a processor, memory (e.g., RAM, flash memory, and/or a hard disc), various wired and wireless interfaces (e.g., Bluetooth, IEEE 802.11, Ethernet, USB, USB-C, and/or proprietary ports such as Apple Lightning), input devices (e.g., touchscreen, keyboard, mouse), and a display. Computing device 120 may operate programmable instructions stored locally or remotely to perform disclosed processes.

Computing device 120 may interact with one or more sensor devices. Computing device 120 may receive sensor data from sensor device 110, sensor device 110B, and/or sensor device 110N. For example, sensor device 110 may send, in real-time, data perceived from sensors. Sensor data may be high-resolution data, and the connection between sensor device 110 and computing device 120 may be a high-bandwidth connection, such as a Bluetooth "classic" wireless connection. While such high-bandwidth wireless technologies may use more power than alternatives (e.g., Bluetooth "low energy"), the increased data resolution that may be used by system 100 may require higher bandwidth wireless interfaces.

System 100 may include controlled device(s) 150 that perform functions based on received instructions. For example, controlled device(s) 150 may include output devices, such as remote displays, speakers, and tactile engines that provide feedback to a user of sensor device 110. These types of controlled devices may provide a status indicator to the user based on the sensor data, such as informing the user that the sensor device is providing a data profile that meets expectations by displaying a green light, playing a positive tone, or tapping the user via a worn tactile engine.

In another example, controlled device(s) 150 may include devices that affect a user's workout environment. For example, controlled device(s) may include a fan, air conditioning system, or workout equipment. In this example, computing device 120 may transmit instructions to increase a fan speed and/or activate an air conditioner responsive to determining that the sensor device 110 indicates that a user's body temperature exceeds a healthy threshold level.

In still other examples, controlled device(s) 150 may include medical devices, such as insulin pumps, pacemakers, cardiac defibrillators, gastric stimulators, deep brain neurostimulators, and/or cochlear implants. In one example, computing device 120 may transmit a control signal to an insulin pump to vary insulin dosage based on data from sensor device 110 indicating higher levels of activity (e.g., a data profile matching an event model for intensifying activity). In another example, computing device 120 may transmit a control signal to a medication pump to provide medication to prevent or greatly lessen Parkinsonian tremors.

System 100 may include network 140. In some embodiments, network 140 may be a wired and/or wireless network. For example, network 140 may be a LAN, WAN, WLAN, or the Internet. System 100 may use network 140 to connect various devices. For example, computing device 120 may connect to server 130, controlled device(s) 150, and/or sensor device 110 using the network. Alternatively, as depicted, computing device 120 may interface directly with sensor device 110 and/or controlled device(s) 150. For example, computing device 120 may form its own wireless access point to connect to other devices.

System 100 may include server 130 to provide networked storage and analysis. Server 130 may be a networked computer. Server 130 may include a central processing unit, such as at least one data processor that executes program components for executing user- or system-generated requests. The processor may include specialized processing units or a general purpose microprocessor.

Server 130 may facilitate network-based (e.g., "cloud") storage and data interaction. For example, computing device 120 may transmit data profiles and the underlying raw data to server 130 for storage. In an embodiment, server 130 may analyze data profiles over time and provide feedback based on changes. Server 130 may transmit notifications (e.g., send email, upload data, revise websites, update databases) based on analysis of data.

In some embodiments, server 130 may serve as a portal to allow users to interact with archived data profiles and raw data. For example, server 130 may provide a graphical user interface that presents data profiles organized by particular categories, dates, or types.

Figure 2:
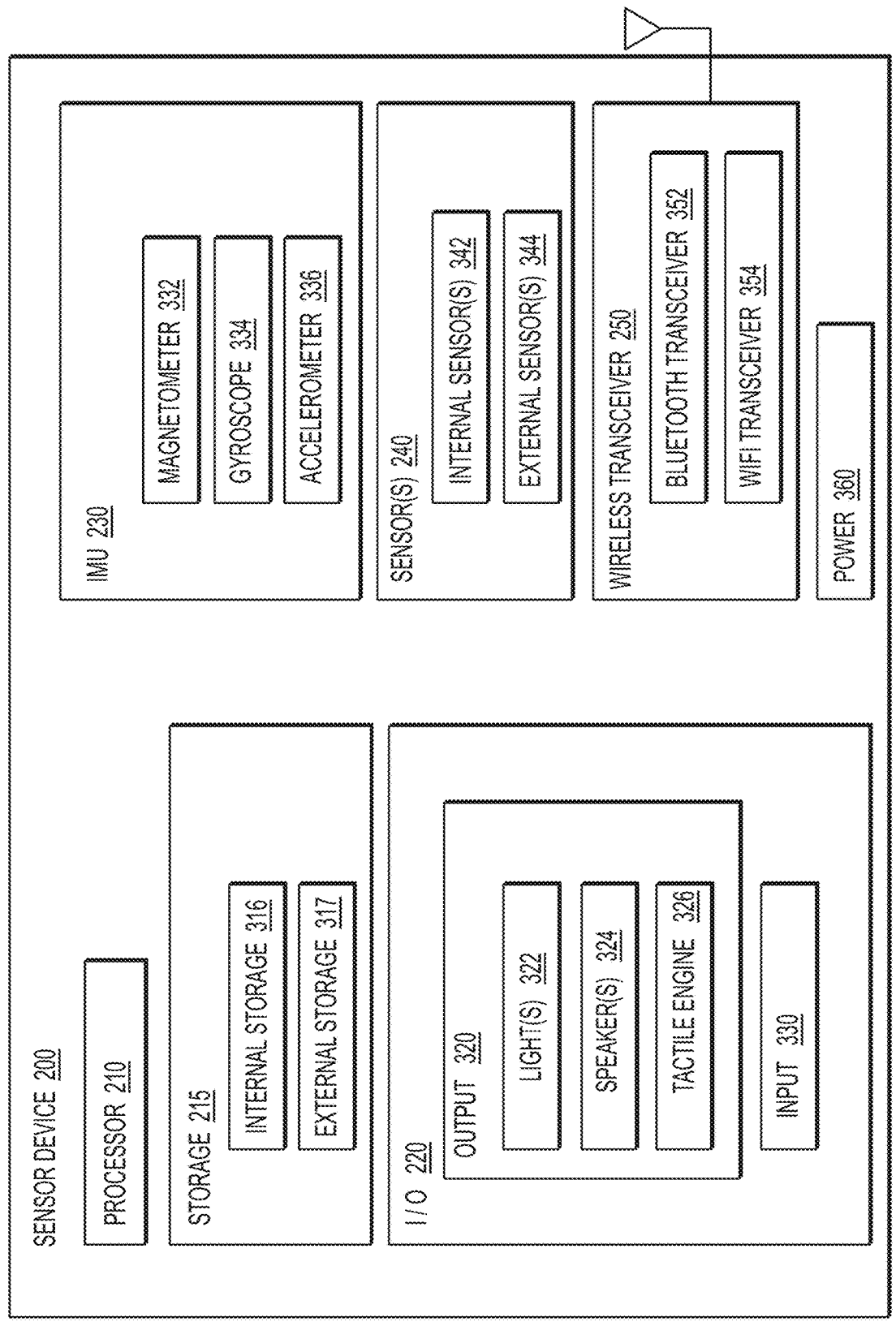
FIG. 2 is a functional block diagram of a sensor device according to some embodiments of the present disclosure.

FIG. 2 is a functional block diagram of sensor device 200 according to some embodiments of the present disclosure. Sensor device 200 may be an example of sensor device 110, consistent with disclosed embodiments. Sensor device 200 may include processor 210, storage 215, input-output 220, IMU 230 (inertial measurement unit), sensor(s) 240, wireless transceiver 250, and/or power 360.

In some embodiments, processor 210 may be a general purpose processor, programmable microcontroller, programmable processor (e.g., a field-programmable gate array (FPGA) or complex programmable logic device (CPLD)), or an application specific integrated circuit (ASIC).

In some embodiments, storage 215 may include internal storage 316 and/or external storage 317. Internal storage 316 may include, for example, on-board memory, such as flash memory or RAM. External storage may include, for example, removable memory media, such as compact flash cards, secure digital cards, memory sticks, optical disks, and the like. In some embodiments, storage 215 may include non-transitory computer-readable media that stores instructions that, when executed by a process (e.g., processor 210), cause the processor to perform disclosed functions and processes.

Input-output 220 may include output 320 and input 330. In some embodiments, output 320 may include lights 322 (e.g., on or more LEDs, an LCD display, a laser, a projector), speaker(s) 324 (e.g., a piezoelectric speaker, a buzzer, a siren, a loudspeaker), and tactile engine 326 (e.g., vibrators, haptic feedback mechanisms). Lights 322 may include lights on various surfaces and different angles of sensor device 200.

Input 330 may allow a user to activate and interact with sensor device 200. In some embodiments, input 330 may include a physical input mechanism (e.g., button, switch, capacitive interface) or a way to receive input (e.g., an infrared receiver, an optical receiver, a USB or serial port). Physical input mechanisms, for example, may allow the user to turn sensor device 200 on and off, synchronize with a computing device, and/or change modes.

Figure 3B:
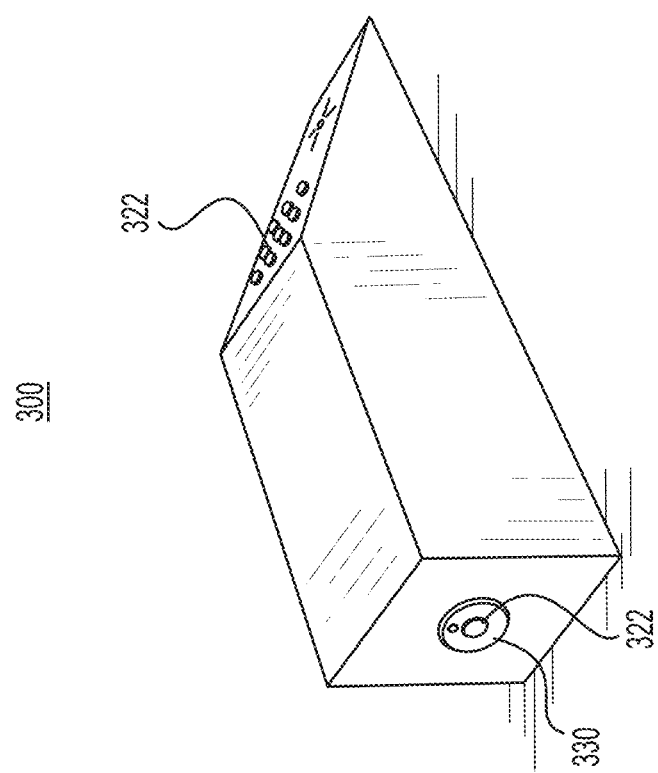
FIGS. 3A and 3B illustrate views of a sensor device in accordance with some embodiments of the present disclosure.
Figure 3A:
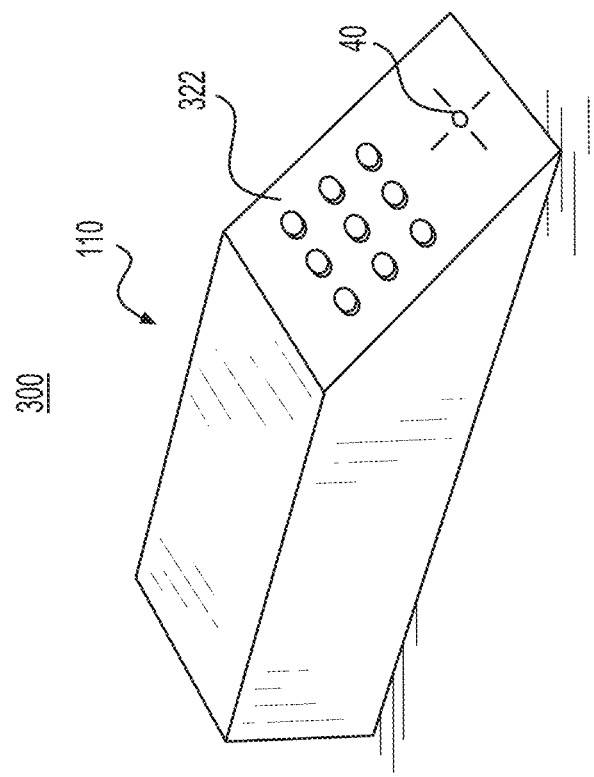

As an example of types of arrangements of output 320 and input 330, FIGS. 3A and 3B illustrate views of sensor device 300 (e.g., an exemplary sensor device 110 and/or sensor device 200) in accordance with some embodiments of the present disclosure. In some embodiments, sensor device 300 may include a combination of lights, such as an LED array. For example, as shown, sensor device 300 includes an angled face with a grid of lights 322 (e.g., LEDs). This grid may be programmed to display low resolution patterns or provide greater intensity light as a single unit. On another face, sensor device 300 may include a light combined with an input device (e.g., light(s) 322 combined with input 330 on the opposite face of sensor device 300). For example, input 330 may be a physical button that a user may press to interact with sensor device 300. Various depression patterns (e.g., long-press, double-press, triple-press, quick-press) may be used to indicate different input codes. For example, a user may long press the button to initiate pairing with a computing device 120. In another example, a user may tap a code corresponding to a tag that the user wishes to associate with a particular set of data collected. The user may, for example, triple tap input 330 before and/or after performing a motion to indicate that system 100 should flag the corresponding motion profile as an "ideal" or template motion, or a particular motion of interest for further analysis (e.g., bookmarking). While input 330 is shown as a single button, additional buttons (not shown) may be placed adjacent to input 330 or on different faces of sensor device 300. In addition to physical buttons, sensor device 300 may include receiver 40 to receive infrared or optical input, for example.

Returning to FIG. 2, in some embodiments, sensor device 200 may include IMU 230 to capture multi-dimensioned acceleration and orientation data. IMU 230 may include magnetometer 332, gyroscope 334, and/or accelerometer 336. In certain embodiments, processor 210 may sample IMU acceleration and orientation data at a rate of 100 samples per second. In some embodiments multiple IMU devices may be "stacked" and then time sliced to permit N Factor sample rate increases such that two such devices can generate 200 samples per second or even more.

In some embodiments, sensor device 200 may include multiple instances of IMU 230 as a redundant measure to filter outlying measurements. For example, processor 210 may receive three-axis acceleration data from two or more IMUs. Processor 210 may average the acceleration data to increase accuracy, or when there are three or more IMUs, processor 210 may not make use of the highest and lowest readings, averaging the remaining readings to reduce measurement inaccuracies.

Although depicted as a single IMU 230, in some embodiments, sensor device 200 may include one or more IMUs combined with additional sensors (e.g., one or more gyroscopes, one or more magnetometers, one or more accelerometers, or any combination thereof). For example, sensor device 200 may integrate measurements from a plurality of IMUs to increase accuracy and reduce jitter. Additionally or alternatively, sensor device 200 may use one or more IMUs to correct drift of standalone gyroscopes or magnetometers, jitter of standalone accelerometers, or the like. Accordingly, devices such as sensor device 200 may exhibit increased accuracy compared to existing devices.

Sensor device 200 may also include various sensor(s) 240. In some embodiments, sensors may be embedded in sensor device 200 as internal sensor(s) 342. For example, a temperature sensor, light intensity sensor, humidity sensor, elevation sensor, and/or microphone may be housed within sensor device 200 and may interface directly with processor 210. In some embodiments, sensors may interface with sensor device 200 through a port or physical interface as external sensor(s) 344. For example, through a USB or serial connection, sensor device 200 may receive data from off-board sensors, such as biopotential telemetry measurement devices (e.g., electrocardiogram (ECG), electroencephalogram (EEG), electromyogram (EMG) data), optical input devices (e.g., cameras, rangefinders), and/or smartphone sensors (e.g., smartphone GPS, elevation, time, weather, sound, light). In some embodiments, external sensor(s) 344 may be used to verify data from internal sensor(s) 342.

Sensor device 200 may include wireless transceiver 250. Transceiver 250 may facilitate communication with computing device 120, network 140, and/or controlled device(s) 150. In some embodiments, transceiver 250 may include Bluetooth transceiver 352 and/or Wi-Fi transceiver 354. In an example, Bluetooth transceiver 352 may be a Bluetooth "classic" transceiver, rather than a Bluetooth "low energy" transceiver in order to provide increased bandwidth to transmit high resolution sensor data (e.g., to computing device 120) in real-time. In another example, Wi-Fi transceiver 354 may be an IEEE 802.11a/b/g/n/x transceiver. Additional wired and/or wireless standards may be used consistent with the bandwidth requirements of the disclosed systems and processes.

Sensor device 200 may include power 360 to provide electricity to components, such as processor 210 and storage 215, among other elements. In some embodiments, power 360 may include a direct current power source, such as a battery. For example, power 360 may include a lithium ion polymer (LiPo) battery, nickel-metal hydride (NiMH) battery, and/or a nickel-cadmium battery. When power 360 includes a battery, power 360 may further include recharging circuitry, such as an electrical port, a removable battery, and/or inductive charging circuitry.

FIGS. 4A, 4B, 4C, and 4D illustrate different equipment with a sensor device according to some embodiments of the present disclosure.

Figure 4A:
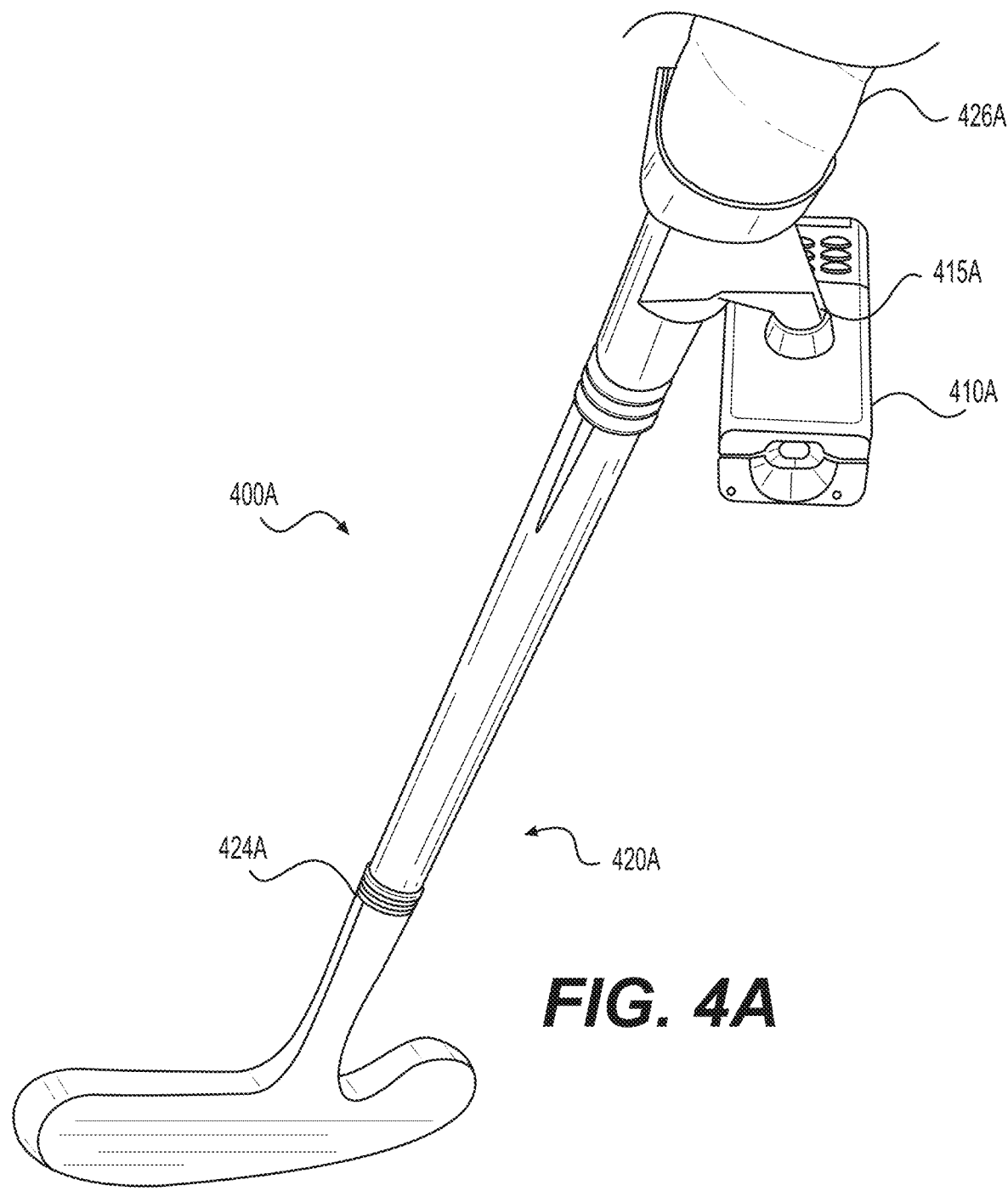

Turning to FIG. 4A, system 400A includes golf club 420A with sensor device 410A. Golf club 420A may be a conventional golf club, such as a putter, driver, or pitching wedge. Golf club 420A may include head 424A and grip 426A.

Sensor device 410A (e.g., sensor device 110) may attach to golf club 420A. In some embodiments, mount 415A may be used to secure sensor device 410A to golf club 420A. While a golf putter is shown, additional club heads, such as drivers, fairway woods, hybrid clubs, irons, and pitching wedges may all serve as golf club 420A. As shown, sensor device 410A may connect to golf club 420A at the base of grip 426A. This positioning of sensor device 410A may advantageously provide more accurate inertial data of the swing motion. For purposes of this discussion, "swing" may refer to the motion of teeing off with a driver, swinging a nine iron on a fairway, and/or putting with a putter, for example. Additionally, placement at the base of grip 426A may allow users to swing golf club 420A without sensor device 410A interfering with their line of sight. However, in other embodiments, sensor device 410A may be mounted at other position on golf club 420A. In still other embodiments, multiple sensor devices may be mounted at different positions of golf club 420A, such as near head 424A, along the shaft, and/or at various locations on grip 426A.

In an embodiment, grip 426A may capture pressure data through the use of pressure sensors. For example, grip 426A may include one or more embedded, attached, or otherwise added pressure sensors. The pressure sensors may record the pressure of the user's grip during use of the club. Such data may be useful in providing relevant, real-time feedback to users while practicing. For example, the grip sensors may also include a feedback mechanism (e.g., tactile engine, light, or speaker) that notifies a user when he or she is gripping the club too tightly, which may negatively impact one's swing. This notification may occur at the exact moment that the pressure sensors sense the club is being gripped too tightly, for example, prior to swinging and/or during a golf swing. Alternatively, the feedback mechanism may be programmed to notify a user that the user's grip was too tight after completion of a golf swing, either automatically, or in response to a user request for feedback and/or sensor data.

To provide the data to system 100, such pressure sensors may form an independent sensor device (e.g., a version of sensor device 110). For example, the grip sensor may independently transmit data over a wireless connection (e.g., a Bluetooth connection) to computing device 120. Similarly, an independent grip sensor device may participate in a sensor mesh network to send data through system 100. Alternatively, the grip sensor(s) may interface with sensor device 410A (e.g., as one or more external sensor(s) 344) to provide the grip pressure data to system 100. For example, the grip sensor may transmit data to processor 210 for handling via an external sensor interface in sensor device 110.

Figure 4B:
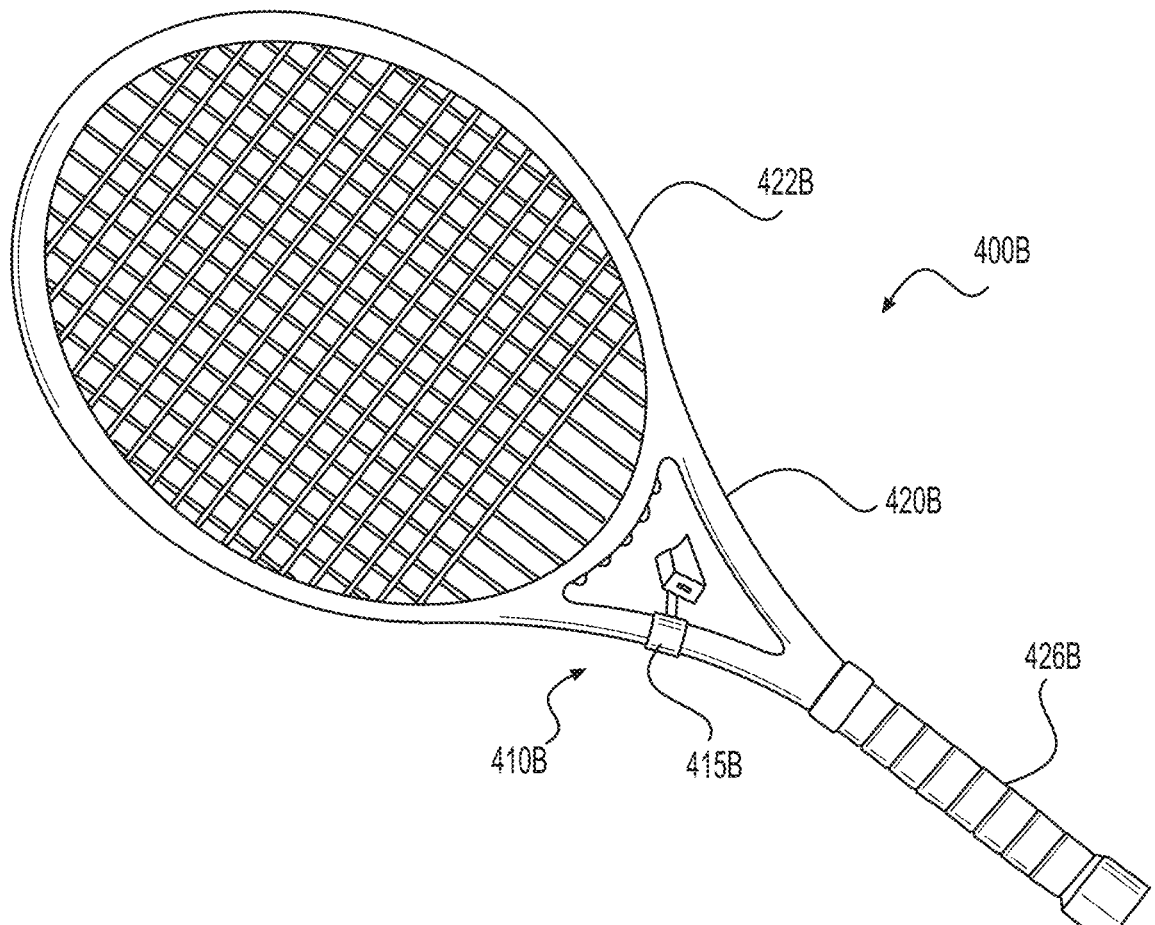

Turning to FIG. 4B, system 400B may include racket 420B with sensor device 410B. Racket 420B may be a conventional racket with head 422B and grip 426B.

Similar to system 400A, in system 400B, sensor device 410B (e.g., sensor device 110) may attach to racket 420B. In some embodiments, mount 415B may be used to secure sensor device 410B to racket 420B. As shown, sensor device 410B may connect to racket 420B between grip 426B and head 422B. This positioning of sensor device 410B may advantageously "hide" sensor device 410B from the line of sight of the user while he or she operates racket 420B. In still other embodiments, sensor device 410B may be mounted at a different position on racket 420B, such as at the top of head 422B, along the shaft, and/or on grip 426A.

Further, as explained above with regard to grip 426A of FIG. 4A, grip 426B may include one or more sensors to measure a user's grip. For example, one or more sensors may measure pressure on grip 426B from the user holding racket 420B, such as generating a pressure map of the user's grip. This may advantageously allow system 100 to determine how the user is holding racket 420B including, for example, determining the relative angle of the face of head 422B relative to the hand or hands of the user. This may allow system 100 to evaluate how the grip angle (e.g., angle with regard to the rotation of the axis of the grip) and pressure affects, for example, serve speed, placement, and spin.

In FIG. 4C, system 400C may include fishing rod 420C and sensor device 410C. Fishing rod 420C may be a conventional fishing pole (e.g., for fly fishing or deep sea fishing. As shown, fishing rod may include reel 428C and handle 426C. Although not explicitly shown, fishing rod 420C may include additional lures and additional guides along the ferrule.

Similar to system 400A, in system 400C, sensor device 410C (e.g., sensor device 110) may attach to fishing rod 420C. In some embodiments, mount 415C may be used to secure sensor device 410C to fishing rod 420C. As shown, sensor device 410C may connect to fishing rod 420C where handle 426C meets the ferule. This positioning of sensor device 410C may advantageously place sensor device 410B out of areas where an angler typically manipulates fishing rod 420C. For example, the depicted sensor device placement allows a user to freely operate reel 428C and does not interfere with the line. In still other embodiments, sensor device 410C may be mounted at a different position on fishing rod 420C, such as along the rod or ferrule, or integrated into reel 428C or handle 426C.

Further, as explained above with regard to grip 426A of FIG. 4A and grip 426B of FIG. 4B, handle 426C may include one or more sensors to measure a user's grip. For example, one or more sensors may measure pressure on handle 426C from the user holding handle 426C. This may advantageously allow system 100 to determine how stiffly the user is holding fishing rod 420C for evaluating how the grip and pressure affects casting technique.

Additionally, while not shown in FIG. 4C, fishing rod 420C may have additional sensors, either embedded or mounted) to measure action of reel 428C and/or tension in the fishing line. Further, sensor devices may be embedded in the hook or fly at the end of the fishing line. Based on this additional data system 100 may generate a data profile that correlates the casting motion (e.g., from IMU data of sensor device 410C) with reel action, line tension, and fly movement. These combined timewise variables may be used to provide real-time feedback to a user to improve casting motions. For example, system 100 may activate a light or vibration to indicate to the user that the cast motion is too aggressive or oscillates too quickly. Additional combinations of sensors and resulting data may be used consistent with the disclosed embodiments to provide additional user feedback and analysis.

Figure 4D:
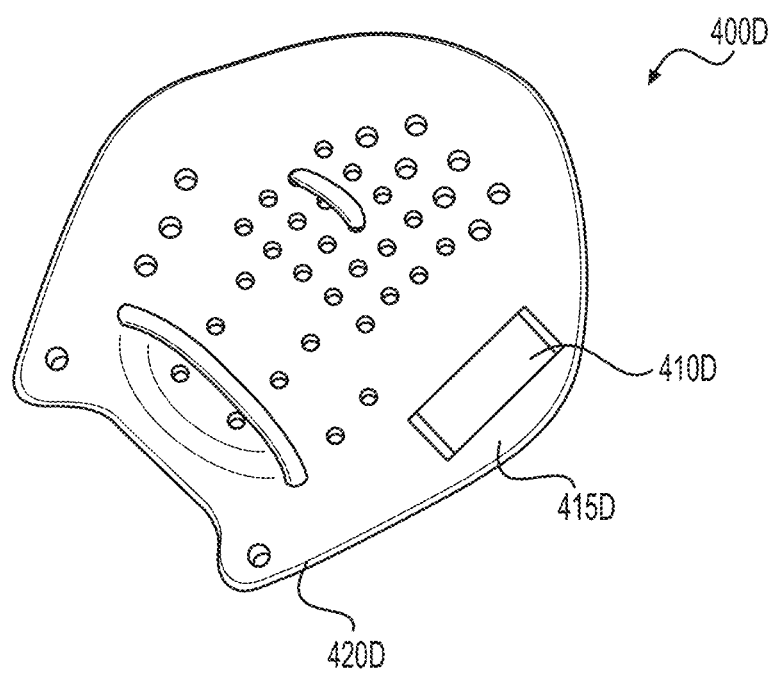

Turning to FIG. 4D, system 400D may include paddle 420D and sensor device 410D. As shown, paddle 420D may be swimming paddle with bands to mount to a swimmer's hand. However, paddle 420D may also be a paddle oar for boating, such as a canoe, stand-up paddleboard, or crew rowing.

In system 400D, sensor device 410D (e.g., sensor device 110) may attach to paddle 420D. In some embodiments, mount 415D may be used to secure sensor device 410D to paddle 420D. Alternatively, sensor device 410D may be integrated into paddle 420D.

Additionally, while not shown, additional sensor units may be used. For example, additional sensors may measure the pressure of water or the user's hand or against a face of paddle 420D. Such sensor data may be used to generate a pressure map of the face of paddle 420D. Based on the sensor data, system 100 may provide feedback on the orientation of paddle 420D during a stroke. For example, in the context of crew rowing, the paddle may be less efficient when its face is not held perpendicular to the direction of the row. The calculated pressure map may reveal points at which the water is not being effectively pulled (or pushed), and system 100 may provide user feedback to adjust the orientation to provide maximum pulling (or pushing) power in the water.

While not shown in FIGS. 4A through 4D, sensor device 110 may be attached to other equipment, such as apparel (e.g., belts, bracelets, shirts, shoes), walking assistance devices (e.g., canes, walkers, scooters, crutches), prosthetics (e.g., hand, arm, leg prosthetics), tools (e.g., hammer, spatula, scalpel), and/or fitness equipment (e.g., medicine balls, jump ropes, helmets, elastic bands).

Figure 5:
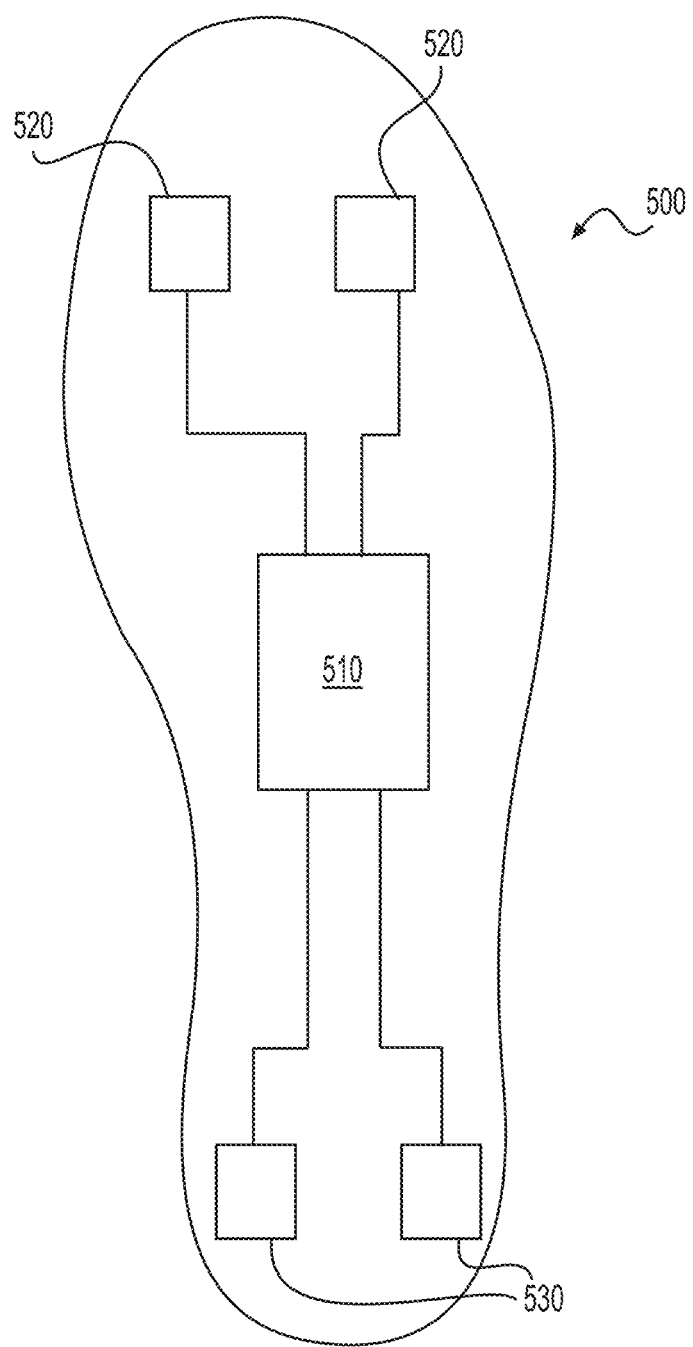
FIG. 5 is a block diagram for a footwear sensor device according to some embodiments of the present disclosure.

FIG. 5 is a block diagram for a footwear sensor device system 500 according to some embodiments of the present disclosure. As shown, sensor device 510 (e.g., sensor device 110) may be embedded into an insole or in a flat flexible sheet that fits below an insole in footwear.

In some embodiments, various pressure sensors may interface with sensor device 510. As shown, toe sensor devices 520 and heel sensor device 530 may connect to sensor device 510 (e.g., as external sensor(s) 344). As shown, four pressure sensors may be located at each corner of system 500 to determine pressure in two-dimensions. Based on the multi-dimensional pressure data, system 100 may generate a pressure map, and provide feedback to the user in real-time to improve stride, gait, pronation, and cadence. For example, various parts of output 320 may be used to indicate to the user that cadence should increase or to shorten stride length, while one is running or walking. Additionally or alternatively, system 100 may generate one or more balance scores (e.g., a composite score, a left score, a right score, or the like) indicating quality of a user's balance, as described in greater detail below.

Although depicted as attached near a foot in FIG. 5, sensor device system 500 may instead be attached near a knee, an elbow, any other joint, a head, or the like. For example, sensor device system 500 may be integrated with a hat or other headwear such that balance indices determined by the device are relative to a central axis of the user's body.

Figure 6:
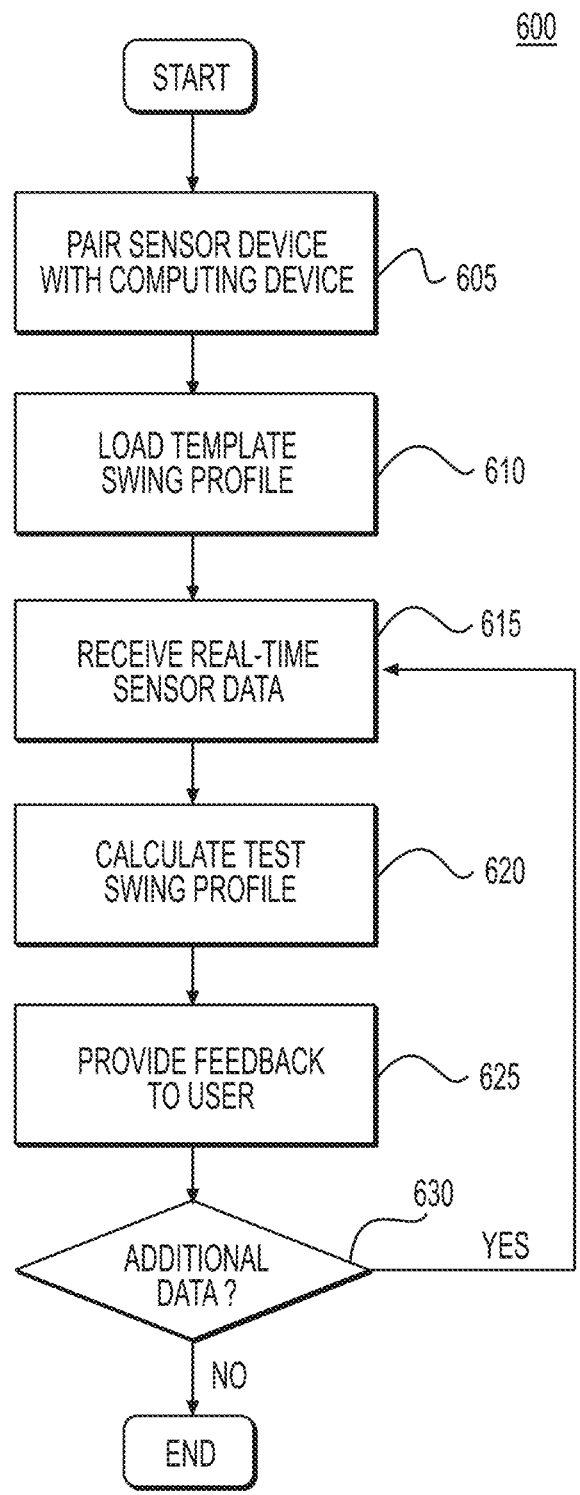
FIG. 6 is a flow diagram illustrating a real-time data acquisition and feedback process in accordance with some embodiments of the present disclosure.

FIG. 6 is a flow diagram illustrating a real-time data acquisition and feedback process in accordance with some embodiments of the present disclosure. Steps in the following discussion may be described with regard to the actions performed by computing device 120. However, one or more alternative devices may instead perform the disclosed functions. For example, in an embodiment, sensor device 110 may perform certain data aggregation, calculation, and/or feedback functions locally (e.g., step 610, step 615, step 620, step 625, and/or step 630). Additionally, while the steps of process 600 are shown in a particular order, the individual steps may be reordered or omitted.

Process 600 may be combined with step 605, where system 100 pairs one or more instances of sensor device 110 with computing device 120. In some embodiments, sensor device 110 may initiate a connection to computing device 120 based on input from a user (e.g., using input 330, such as pressing a button). For example, sensor device 110 may utilize a Bluetooth pairing procedure or connect to computing device 120 via a Wi-Fi connection. In some embodiments, computing device may search or look for sensor devices that are trying to connect or available for connection.

In some embodiments, step 610 may include a calibration procedure. Sensor device 110 may calibrate sensors, such as IMU 230, prior to pairing with computing device 120. For example, sensor device 110 may provide an indication to a user (e.g., a flashing light of lights 322) to indicate to a user to rotate sensor device 110 so that IMU 230 may align its axes and adjust scaling factors to increase accuracy in position and orientation calculations. In other embodiments, calibration may occur during or after pairing, such as when system 100 determines that the data from IMU 230 lacks necessary precision.

In step 610, process 600 may load a template swing profile. The term "swing profile" as used in this disclosure may refer to various golf motions, including swinging a driver, performing a chip shot, and/or putting with a putter, for example. The terms "putt profile" and "swing profile" may be used interchangeably. Computing device 120 may retrieve a data profile (e.g., a motion profile) to serve as a template or pattern for comparing purposes. The data profile may include multi-dimensional acceleration and/or orientation data corresponding to a golf swing. In an embodiment, the template swing profile may be recalled from local or network storage. For example, computing device 120 may request a particular template swing profile from server 130 or other cloud storage.

In an embodiment, loading a template swing profile (step 610) may include recording one or more motion profiles for an actual swing. For example, a user may provide an initial motion at the start of a practice session that acts as a template and may want to practice repeating that initial, template motion. To record an initial template motion, system 100 may receive sensor data from sensor device 200 that is recorded during the swing motion. For example, IMU 230 may record acceleration and/or orientation data along three or fewer axes during a particular swing motion. Sensor device 110 may transmit the IMU data to computing device 120, which may, in turn, store the IMU data for the swing motion as a motion profile. For example, the "ideal" template swing may be recorded in a clinical setting, such as with a trainer, and later recalled when a user practices without the trainer nearby.

In an embodiment, step 610 may include recording a motion, generating the template, storing the template in a networked server (e.g., server 130), and/or requesting the stored template for networked storage. In still further embodiments, step 610 may include receiving a motion profile that is generated from a software application, rather than recorded from a live motion. For example, in step 610, computing device 120 may receive a motion profile generated by process 1100, which is described later in this specification and depicted in FIG. 11. Additional combinations or intermittent processes may be used such that computing device 120 receives a data profile or a motion profile for use consistent with the remaining steps of process 600.

In step 615, process 600 may receive real-time sensor data. Computing device 120 may receive real-time data from sensor device 110. In some embodiments, computing device 120 may receive sensor data in real-time over a wireless transmission technology such as Bluetooth or Wi-Fi (e.g., using Bluetooth transceiver 352 and/or Wi-Fi transceiver 354). Computing device 120 may receive packets of data containing real-time data samples from one or more of internal sensor(s) 341 and/or external sensor(s) 344. For example, computing device 120 may receive one or more packets containing 1-10 samples of data for a given sensor over an interval of 1-5 milliseconds, with less than a 5 millisecond delay from capture by sensor device 110. The samples may be stored as time-value pairs in an array, such as sensor sample values paired with timestamp values in a list. In some embodiments, computing device 120 may continue to receive sensor data packets so long as sensor device 110 captures relevant data (e.g., as discussed with regard to step 810, step 820, and/or step 830 of FIG. 8 below).

In step 620, process 600 may calculate a test swing profile. Computing device 120 may aggregate received sensor data into a combined time-wise arrangement of sensor readings. In some embodiments, computing device 120 may create a new data structure organizing the sensor data for a given motion. The data structure may store an abbreviated form of raw sensor data with standardized metadata in a data object. For example, computing device 120 may receive raw sensor data having varying fidelity (e.g., differing sample rates and/or data precision). Computing device 120 may organize data such that the resulting class of data structures has consistent sampling rates and/or sample data with consistent resolution (e.g., values having the same number of significant figures). For example, computing device 120 may down-sample sensor data having a sampling rate greater than the standardized sampling rate or range of sampling rates for a given class or type of swing profile (e.g., a type of motion profile) data structures. For received sensor data having a sampling rate that is lower than a minimum sampling rate for a given class of swing profiles, computing device 120 may interpolate additional data points to achieve the desired sampling rate (e.g., using curve fitting or regression analysis).

In some embodiments, the swing profile (e.g., a data profile or motion profile) may include standardized metadata. For example, the swing profile class may include fields for standardized data analysis variables, such as mean and median values of the sensor data, as well as standard deviation, high value, low value, local minima and maxima, and points of inflection. Additional data analytics discussed throughout this disclosure may be stored as part of the swing profile.

In some embodiments, the calculations may include comparing the test swing profile to a reference profile, such as the template swing profile (e.g., from step 610). Computing device 120 may compare the two profiles to determine where the two profiles deviate and how much the two profiles deviate. In an embodiment, computing device 120 may generate a profile indicating the differences over time. Additional comparisons may be made consistent with the data profile and motion profile comparisons discussed in this disclosure.

In step 625, process 600 may provide feedback based on the calculations made in step 620. Feedback may include visual, tactile, and/or auditory signals directed to a user and/or third party. The feedback may be based on the calculated test swing profile, its associated metadata, or a comparison based on the same. The calculations from step 620 may act as triggers for feedback. For example, when a test swing profile deviates more than a predefined amount, system 100 may generate feedback. In another example, system 100 may generate feedback when the test motion profile matches certain criteria, such as an average or standard deviation value. Such values may be user-defined or pre-defined (e.g., from loading a template profile in step 610). Feedback may be provided to a user between 5 and 20 milliseconds from receiving the data from the sensors, for example.

In some embodiments, computing device 120 may provide feedback to a user. For example, computing device may generate a graphical user interface that displays an analysis of sensor data. Additionally or alternatively, computing device 120 may generate one or more balance scores (also referred to as "indices") based on the sensor data, as discussed below with respect to FIGS. 10 and 11.

Figure 7:
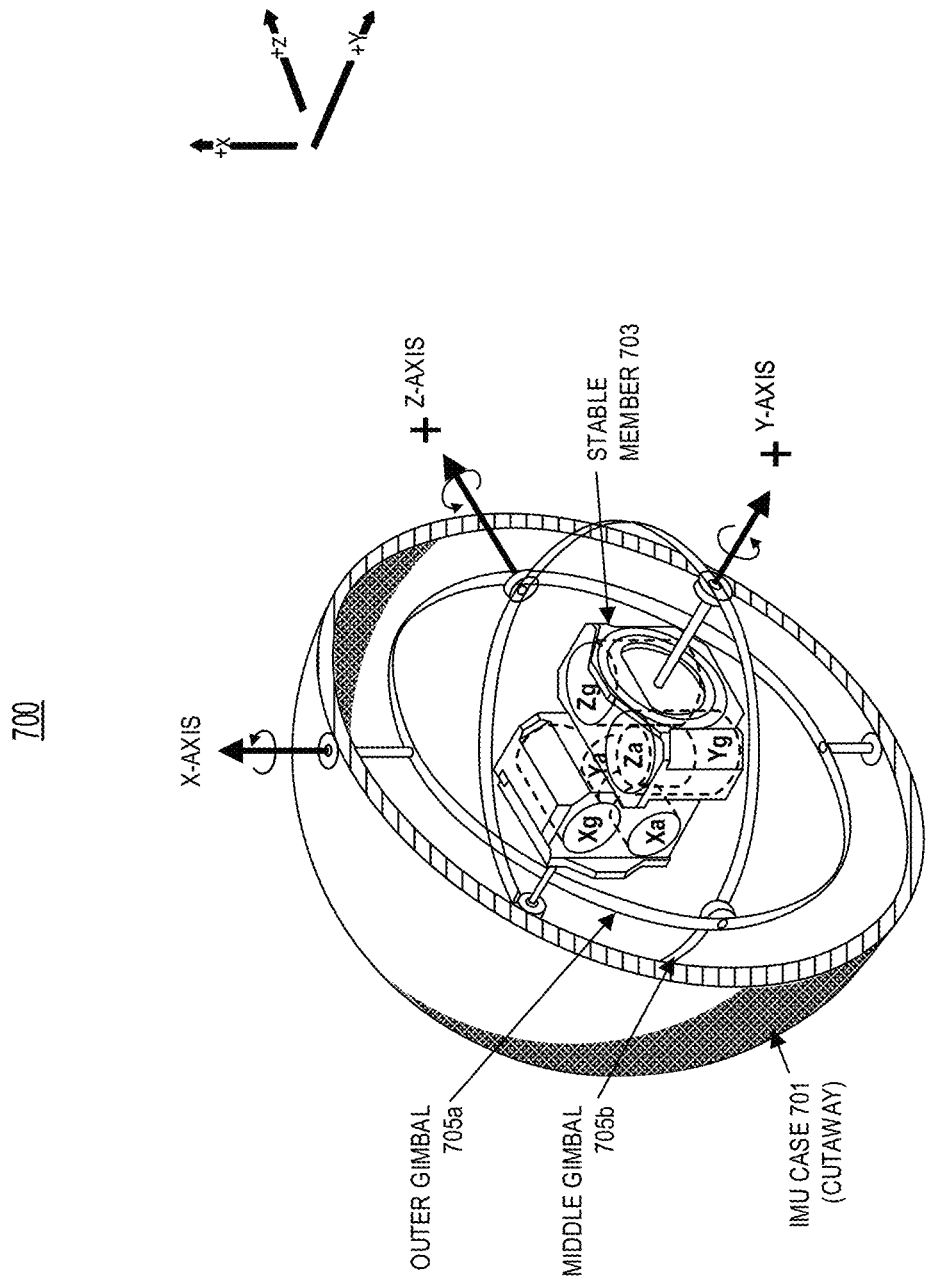
FIG. 7 illustrates an example inertial measurement unit (IMU) in accordance with some embodiments of the present disclosure.

FIG. 7 illustrates an example inertial measurement unit (IMU) for capturing sensor data according to some embodiments of the present disclosure. As depicted in FIG. 7, IMU 700 includes a stable element 703 enclosed by a plurality of gimbals (e.g., outer gimbal 705a and middle gimbal 705b) and encased within a case 701. For example, case 701 may comprise a plastic, metal, or other hard material protecting stable element 703 and its corresponding gimbals from external environmental factors. IMU 700 may further comprise an integrating gyroscope (also referred to as a "gyro") for each axis (labeled $X_g$, $Y_g$, and $Z_g$ in FIG. 7) and an integrating accelerometer for each axis (labeled $X_a$, $Y_a$, and $Z_a$ in FIG. 7). Although not depicted in FIG. 7, IMU 700 may further comprise a magnetometer for determining cardinal directions from Earth's magnetic field.

Figure 9:
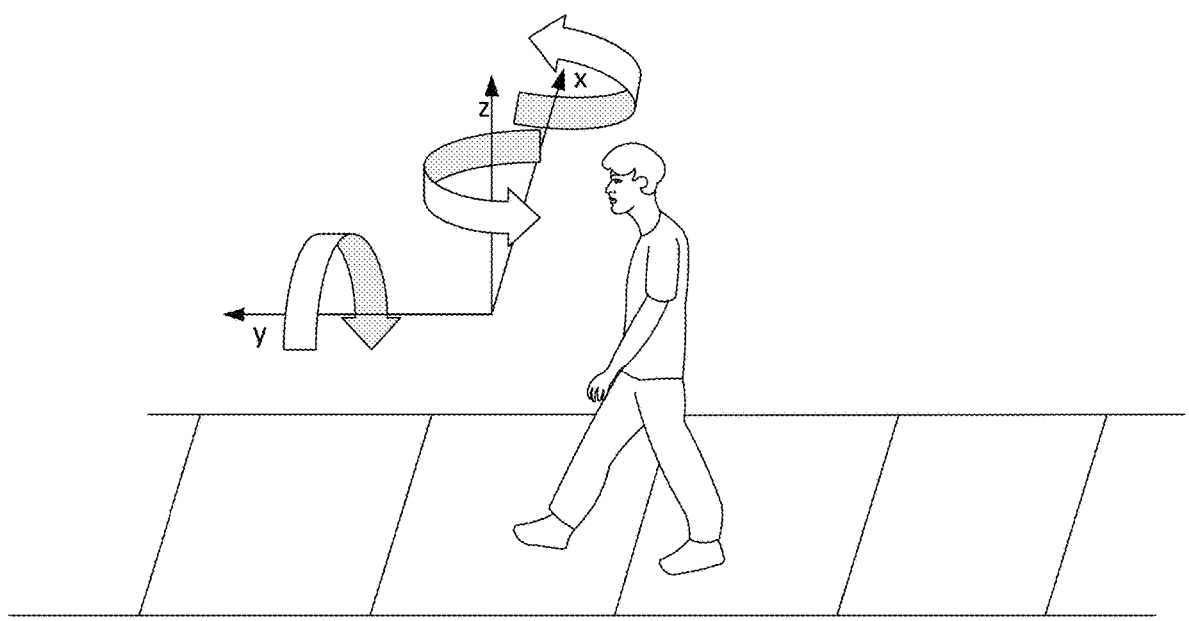
FIG. 9 illustrates an example set of axes for calculating balance measures in accordance with some embodiments of the present disclosure.

Accordingly, IMU 700 may measure angular velocity changes of each gyro for determining magnitudes of deviations along the x-axis, y-axis, and z-axis. Moreover, IMU 700 may measure accelerations of each accelerometer for determining velocities along the deviations measured using the gyros. In embodiments including a magnetometer, IMU 700 may determine a path of IMU 700 as a user of IMU 700 moves from location to location. In some embodiments, IMU 700 may fuse measurements from the magnetometer and/or the accelerometers with measurements from the gyros to determine the deviations along a set of orientation axes (e.g., as depicted in FIG. 9). Additionally or alternatively, IMU 700 may use measurements from the magnetometer to correct drift of the gyros (labeled $X_g$, $Y_g$, and $Z_g$ in FIG. 7). Similarly, IMU 700 may additionally or alternatively use measurements from the gyros (labeled $X_g$, $Y_g$, and $Z_g$ in FIG. 7) to smooth jitter from the accelerometers (labeled $X_a$, $Y_a$, and $Z_a$ in FIG. 7) and/or the magnetometer (if included).

Although not depicted in FIG. 7, IMU 700 may include a wired connection and/or a wireless transmitter (e.g., a Bluetooth® transmitter, a WiFi transmitter, a cellular network, such as 4G or LTE, transmitter, or the like) for sending measurements to a processor. For example, the gyros (labeled $X_g$, $Y_g$, and $Z_g$ in FIG. 7), the accelerometers (labeled $X_a$, $Y_a$, and $Z_a$ in FIG. 7), and the magnetometer (if included) may be wired to the processor. In some embodiments, one or more of the gyros (labeled $X_g$, $Y_g$, and $Z_g$ in FIG. 7), the accelerometers (labeled $X_a$, $Y_a$, and $Z_a$ in FIG. 7), and the magnetometer (if included) may be wired separately. Additionally or alternatively, at least two or more of the gyros (labeled $X_g$, $Y_g$, and $Z_g$ in FIG. 7), the accelerometers (labeled $X_a$, $Y_a$, and $Z_a$ in FIG. 7), and the magnetometer (if included) may be wired in series to the processor.

Figure 8:
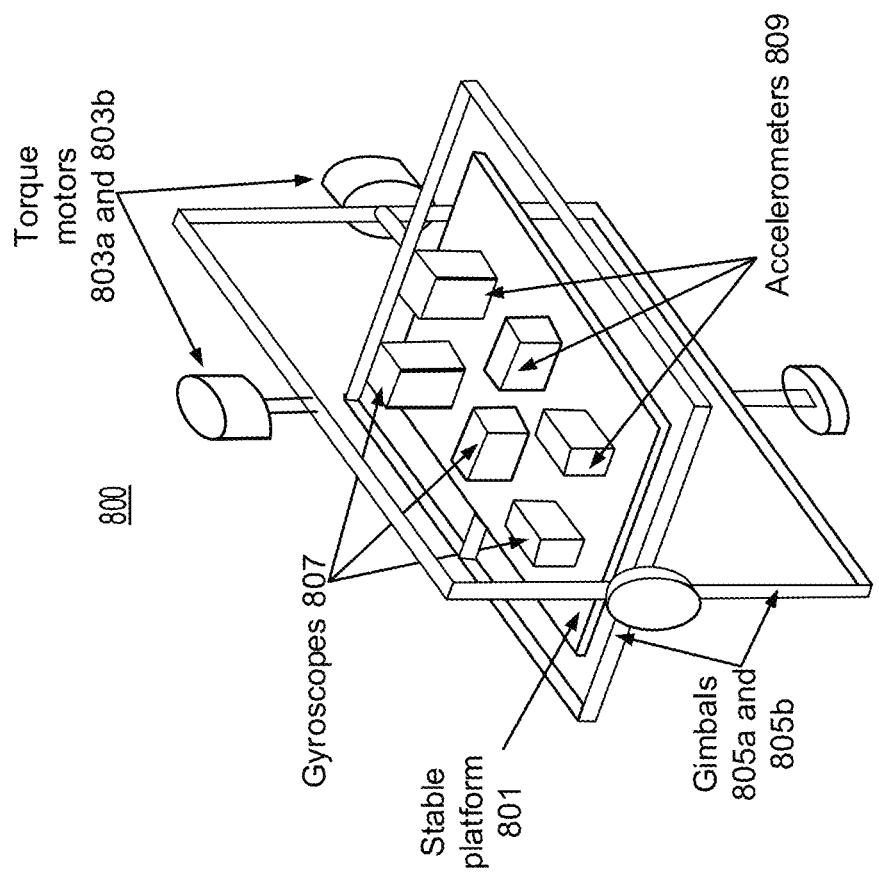
FIG. 8 illustrates another example IMU in accordance with some embodiments of the present disclosure.

FIG. 8 illustrates another example inertial measurement unit (IMU) for capturing sensor data according to some embodiments of the present disclosure. As depicted in FIG. 8, IMU 800 includes a stable platform 801 mounted on a plurality of gimbals (e.g., gimbals 805a and 805b) with corresponding torque motors (e.g., motors 803a and 803b). For example, torque motors 803a and 803b may determine corresponding angular velocity measurements from gimbals 805a and 805b. Additionally or alternatively, torque motors 803a and 803b may apply corrections to stable platform 801, e.g., to correct for drift or other errors.

IMU 800 may further comprise one or more gyroscopes 807 and one or more accelerometers 809 mounted on stable platform 801. Similar to IMU 700 of FIG. 7, the one or more gyroscopes 807 and one or more accelerometers 809 of IMU 800 may correspond to particular axes of IMU 800. Although not depicted in FIG. 8, IMU 800 may further comprise a magnetometer for determining cardinal directions from Earth's magnetic field.

Accordingly, IMU 800 may measure angular velocity changes of each gyroscope for determining magnitudes of deviations along corresponding axes. Moreover, IMU 800 may measure accelerations of each accelerometer for determining velocities along the deviations measured using the gyroscopes 807. In embodiments including a magnetometer, IMU 800 may determine a path of IMU 800 as a user of IMU 800 moves from location to location. In some embodiments, IMU 800 may fuse measurements from the magnetometer and/or the accelerometers with measurements from the gyros to determine the deviations along a set of orientation axes (e.g., as depicted in FIG. 9). Additionally or alternatively, IMU 800 may use measurements from the magnetometer to correct drift of the gyroscopes 807. Similarly, IMU 800 may additionally or alternatively use measurements from the gyroscopes 807 to smooth jitter from the accelerometers 809 and/or the magnetometer (if included).

Although not depicted in FIG. 8, IMU 800 may include a wired connection and/or a wireless transmitter (e.g., a Bluetooth® transmitter, a WiFi transmitter, a cellular network, such as 4G or LTE, transmitter, or the like) for sending measurements to a processor. For example, the gyroscopes 807, the accelerometers 809, and the magnetometer (if included) may be wired to the processor. In some embodiments, one or more of the gyroscopes 807, the accelerometers 809, and the magnetometer (if included) may be wired separately. Additionally or alternatively, at least two or more of the gyroscopes 807, the accelerometers 809, and the magnetometer (if included) may be wired in series to the processor.

The examples shown in FIGS. 7 and 8 are not exclusive. For example, IMUs developed with micro-electro-mechanical systems (MEMS) technology may be used in addition with or in lieu of the IMUs depicted in FIGS. 7 and 8. Still further examples of integrated circuits and sensor devices capable of measuring rotational acceleration, linear acceleration, and orientation can be used, consistent with the disclosed embodiments.

FIG. 9 illustrates an example of axes for one or more IMUs relative to a user with a wearable device including the one or more IMUs. In the example of FIG. 9, the y-axis is aligned with a direction along which the user moves forward and backward. Moreover, in the example of FIG. 9, the x-axis is aligned with a direction along which the user moves left and right. Finally, in the example of FIG. 9, the z-axis is aligned with a direction along which the user moves up and down. The corresponding rotational directions shown in the example of FIG. 9 are right-handed directions for angular rotation about the axes. Accordingly, in lieu of the example of FIG. 9, any set of right-handed axes may be used as a reference for measurements from one or more IMUs. Moreover, in some embodiments, measurements from the one or more IMUs may be relative to one set of right-handed axes and translated (e.g., by a processor) to a different set of right-handed axes. Moreover, although depicted as a right-handed coordinate system, any left-handed coordinate system (with corresponding left-handed directions for angular rotation about the axes) may be used instead.

Figure 10:
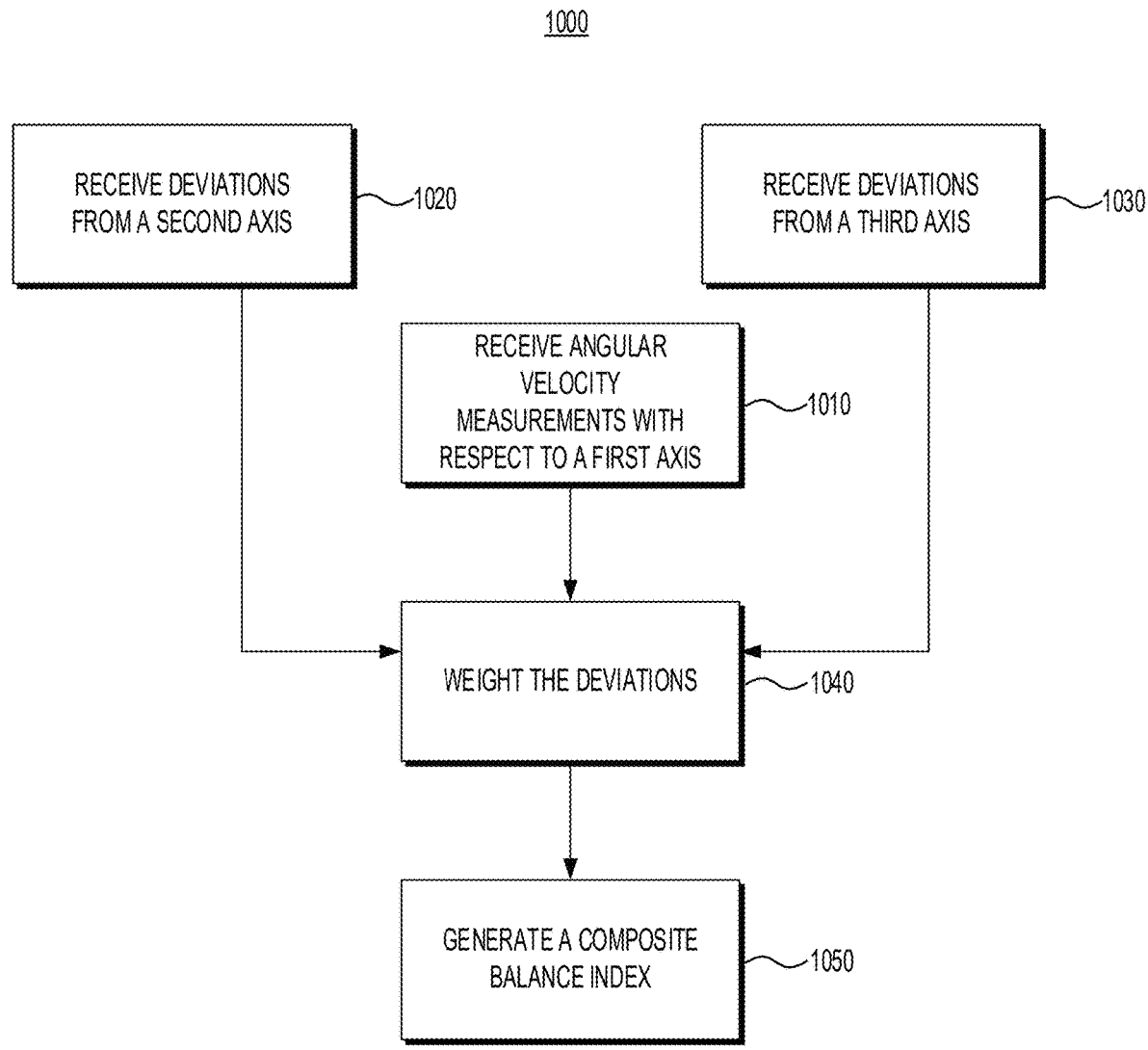
FIG. 10 is a flow diagram illustrating a process for generating a composite balance index in accordance with some embodiments of the present disclosure.

FIG. 10 is a flow diagram illustrating a process for determining balance of a user in accordance with some embodiments of the present disclosure. Steps in the following discussion may be described with regard to the actions performed locally by sensor device 110. However, one or more alternative devices may instead perform the disclosed functions. For example, in an embodiment, computing device 120 may perform certain processing of measurements locally (e.g., step 1040). Additionally, while the steps of process 1000 are shown in a particular order, one or more individual steps may be reordered and/or omitted. For example, certain embodiments of process 1000 may receive additional data after weighting deviations (e.g., step 1040). In another example, no weighting may be performed (e.g., step 1040 is omitted). Still further permutations of functions may be employed consistent with this disclosure.

In step 1010, process 1000 may receive, from at least one gyroscope of sensor device 110, angular velocity measurements over a period of time. For example, the at least one gyroscope may include a gyroscope as depicted in FIG. 7 or 8, a MEMS gyroscope, or any other device configured to measure deviation of a rotating mass, whether included as part of a larger sensor (such as an IMU) or implemented as a standalone device. Accordingly, process 1000 may include receiving signals from the at least one gyroscope. The signals may represent angular velocity about a first axis (e.g., the z-axis of FIG. 9 or any other axis). Alternatively, the signals may represent different variables (e.g., angular acceleration or the like) from which sensor device 110 or computing device 120 may determine angular velocity (e.g., by integrating angular acceleration over time, or any other appropriate calculation). Accordingly, in some embodiments, step 1010 may further include processing signals from the at least one gyroscope to determine the angular velocity.

In step 1020, process 1000 may receive, from at least one IMU of sensor device 110, deviations from a second axis over the period of time. For example, the at least one IMU may comprise IMU 700 depicted in FIG. 7, IMU 800 depicted in FIG. 8, a MEMS IMU, or any other device configured to measure a spatial deviation along the second axis, e.g., using an accelerometer, a gyroscope, a magnetometer, or a combination thereof. Accordingly, process 1000 may include receiving signals from the at least one IMU. The signals may represent deviations along the second axis (e.g., the y-axis or the x-axis of FIG. 9 or any other axis). Alternatively, the signals may represent different variables (e.g., angular velocity, angular acceleration, linear acceleration, or the like) from which sensor device 110 or computing device 120 may determine a spatial deviation (e.g., by integrating linear acceleration over time, or any other appropriate calculation). Accordingly, in some embodiments, step 1020 may further include processing signals from the at least one IMU to determine the deviations.

In step 1030, process 1000 may receive, from the at least one IMU of sensor device 110, deviations from a third axis over the period of time. For example, the at least one IMU may comprise IMU 700 depicted in FIG. 7, IMU 800 depicted in FIG. 8, a MEMS IMU, or any other device configured to measure a spatial deviation along the second axis, e.g., using an accelerometer, a gyroscope, a magnetometer, or a combination thereof. Accordingly, process 1000 may include receiving signals from the at least one IMU. The signals may represent deviations along the third axis (e.g., the y-axis or the x-axis of FIG. 9 or any other axis). Alternatively, the signals may represent different variables (e.g., angular velocity, angular acceleration, linear acceleration, or the like) from which sensor device 110 or computing device 120 may determine a spatial deviation (e.g., by integrating linear acceleration over time, or any other appropriate calculation). Accordingly, in some embodiments, step 1030 may further include processing signals from the at least one IMU to determine the deviations.

Any combination of IMUs may be used for the measurements of steps 1020 and 1030. For example, one IMU may determine deviations along the second axis for step 1020 and a different IMU may determine deviations along the third axis. In such an example, the IMUs may also be used to correct drift of each other's gyroscopes and/or magnetometer. Additionally or alternatively, process 1000 may combine measurements from a plurality of IMUs for the deviations along the second axis and/or for the deviations along the third axis. For example, a plurality of IMUs may measure deviations (or signals otherwise indicative of deviations) along the second axis and/or the third axis such that sensor device 110 or computing device 120 may combine the measurements to determine the deviations with greater accuracy than with a single IMU. In some embodiments, one or more of the IMUs measuring deviations along the second axis and/or deviations along the third axis may also include the at least one gyroscope that measures the angular velocity (or signals otherwise indicative of angular velocity) with respect to the first axis for step 1010. Alternatively, the at least one gyroscope may be separate from (or included in an IMU separate from) the at least one IMU used for steps 1020 and/or 1030.

In step 1040, process 1000 may weigh the deviations from step 1020 and the deviations from step 1030 based on directions associated with the deviations. For example, sensor device 110 or computing device 120 may apply one or more multipliers to the deviations (such as double, treble, or the like). In such an example, different multipliers may apply to different directions. For example, a forward direction may have a multiplier of two (2), and a backward direction may have a multiplier of four (4). Additionally or alternatively, some directions may share a multiplier. For example, a left direction and a right direction may share a multiplier of three (3). Any other multipliers may be used. For example, a forward direction, left direction, and right direction may be associated with a multiplier of one (1) or three (3) while a backward direction may be associated with a multiplier of two (2) or five (5). Thus, changes in a +y direction (as depicted in FIG. 9) may be adjusted to 3*(+y) while changes in a −y direction (as depicted in FIG. 9) may be adjusted to 5*(−y). In this example, the absolute value of the deviation may be multiplied rather than the deviation itself. In another example where a person's dominant side is left, a forward direction may be associated with a multiplier of one (1) or three (3), a left direction may be associated with a multiplier of two (2) or four (4), a right direction may be associated with a multiplier of three (3) or five (5), and a backward direction may be associated with a multiplier of four (4) or six (6). Thus, changes in a −x direction (as depicted in FIG. 9) may be adjusted to 2*(−x) while changes in a +x direction (as depicted in FIG. 9) may be adjusted to 4*(+x). In this example, the absolute value of the deviation may be multiplied rather than the deviation itself. Similarly, in an example where a person's dominant side is right, a forward direction may be associated with a multiplier of one (1) or three (3), a right direction may be associated with a multiplier of two (2) or four (4), a left direction may be associated with a multiplier of three (3) or five (5), and a backward direction may be associated with a multiplier of four (4) or six (6).

In another example, sensor device 110 or computing device 120 may apply one or more powers to the deviations (such as square, cube, or the like). In such an example, different power may apply to different directions. For example, a forward direction may have a power of two (2), and a backward direction may have a power of four (4). Thus, changes in a +y direction (as depicted in FIG. 9) may be adjusted to $(+y)^2$ while changes in a −y direction (as depicted in FIG. 9) may be adjusted to $(-y)^4$. Accordingly, a weight for the second axis or the third axis may be greater for a first direction than a second, opposite direction. Additionally or alternatively, some directions may share a power. For example, a left direction and a right direction may share a power of three (3). Thus, changes in an x direction (as depicted in FIG. 9) may be adjusted to $(x)^3$. In this example, the absolute value of the deviation may be cubed rather than the deviation itself. Accordingly, a weight for the second axis or the third axis may be the same for a first direction and for a second, opposite direction. Any other multipliers may be used. For example, a forward direction, left direction, and right direction may be associated with a power of one (1) or three (3) while a backward direction may be associated with a power of two (2) or five (5). In another example where a person's dominant side is left, a forward direction may be associated with a power of one (1) or three (3), a left direction may be associated with a power of two (2) or four (4), a right direction may be associated with a power of three (3) or five (5), and a backward direction may be associated with a power of four (4) or six (6). Similarly, in an example where a person's dominant side is right, a forward direction may be associated with a power of one (1) or three (3), a right direction may be associated with a power of two (2) or four (4), a left direction may be associated with a power of three (3) or five (5), and a backward direction may be associated with a power of four (4) or six (6).

In some embodiments, the multipliers or powers may be selected based on a placement of the wearable device. For example, the placement may comprise placement on a head, placement on a hip, placement on a neck, or the like. Sensor device 110 or computing device 120 may detect the placement base on one or more measurements or received as input (e.g., from a user and/or over at least one computer network). In such embodiments, the one or more weights associated with at least one of the second axis or the third axis may be greater for the placement on the head or the placement on the neck than the placement on the hip.

In the example of FIG. 9, the forward direction may be associated with a positive direction along the y-axis and the backward direction may be associated with a negative direction along the y-axis. Similarly, the left direction may be associated with a negative direction along the x-axis and the right direction may be associated with a positive direction along the x-axis. Other embodiments using different left- (or right-) handed coordinate axes may associated different axes with the forward direction, the backward direction, the left direction, and the right direction.

In some embodiments, the angular velocities may be weighted based on a standard deviation from plumb over the period of time. Additionally or alternatively, one or more multipliers or power, e.g., as described above, may be used to weight the angular velocities.

In some embodiments, the deviations may be measured in radians. In such embodiments, sensor device 110 or computing device 120 may integrate the angular velocity measurements from step 1010 to calculate radians over the period of time. Additionally or alternatively, sensor device 110 or computing device 120 may integrate the deviations from step 1010 to calculate radians over the period of time. Accordingly, the weighted deviations and angular velocity measurements may be combined in step 1050 without further conversions. In other embodiments, sensor device 110 or computing device 120 may convert the deviations from a spatial unit (e.g., centimeters, meters, or the like) to radians or another dimensionless measurement before weighting and/or combination in step 1050.

In step 1050, process 1000 may generate a composite balance index based on the angular velocity measurements, the weighted deviations from the second axis, and the weighted deviations from the third axis. For example, sensor device 110 or computing device 120 may perform a weighted summation of angular velocities integrated over the period of time and the weighted deviations. In another example, sensor device 110 or computing device 120 may convolve the angular velocities integrated over the period of time with the weighted deviations. In yet another example, sensor device 110 or computing device 120 may multiply the angular velocities integrated over the period of time with the weighted deviations. Any other combinatory technique may be used to generate the composite balance index from the angular velocity measurements, the weighted deviations from the second axis, and the weighted deviations from the third axis.

Accordingly, process 1000 may use sensors from IMUs as follows in Example Table 1, which is not exclusive:

TABLE 1

(exemplary only)

|  | Characteristics | Measurements |
|---|---|---|
| Magnetometer | Translational measurements but jitter reduces accuracy | Localization of user |
| Gyroscope | Accurate angular momentum measurements but drift needs correction | Angular velocity about first axis |
| Accelerometer (in some examples, a gravitometer) | Suffers from ringdown and noise but can correct for jitter and/or drift and increase resolution | Deviations along a second axis and/or a third axis |

For example, sensor device 110 may eliminate any measurements from the accelerometer that do not agree with the gyroscope (e.g., at least within a threshold of error) because such measurements are likely noise or otherwise due to jitter. Additionally or alternatively, sensor device 110 may, at intervals, use one or more torque motors (e.g., 803a and 803b as depicted in FIG. 8) to adjust the gyroscope to align with a position as indicated by the magnetometer to avoid drift of the gyroscope.

In some embodiments, sensor device 110 or computing device 120 may additionally include deviations along the first axis in the composite balance index. For example, sensor device 110 or computing device 120 may include deviations from plumb in the composite balance index. The deviations from plumb may be unmodified or may be modified by a multiplier or power, e.g., as described above with respect to step 1040.

Although not depicted in FIG. 10, process 1000 may further include normalizing the angular velocity measurements over the period of time and/or normalizing the deviations from the second axis and the deviations from the third axis over the period of time (either before weighting or after weighting but before step 1050). For example, sensor device 110 or computing device 120 may normalize using one or more smooth algorithms. Additionally or alternatively, sensor device 110 or computing device 120 may normalize by integrating over time, as described above.

Sensor device 110 or computing device 120 may output the composite balance index to an external device associated with the user, e.g., a smartphone, a tablet, or the like. In some embodiments, sensor device 110 or computing device 120 may also output a graphical depiction of the deviations from the second axis and the deviations from the third axis over the period of time to an external device associated with the user. Sensor device 110 or computing device 120 may transmit the composite balance index and/or the graphical depiction over at least one wireless network.

Figure 11:
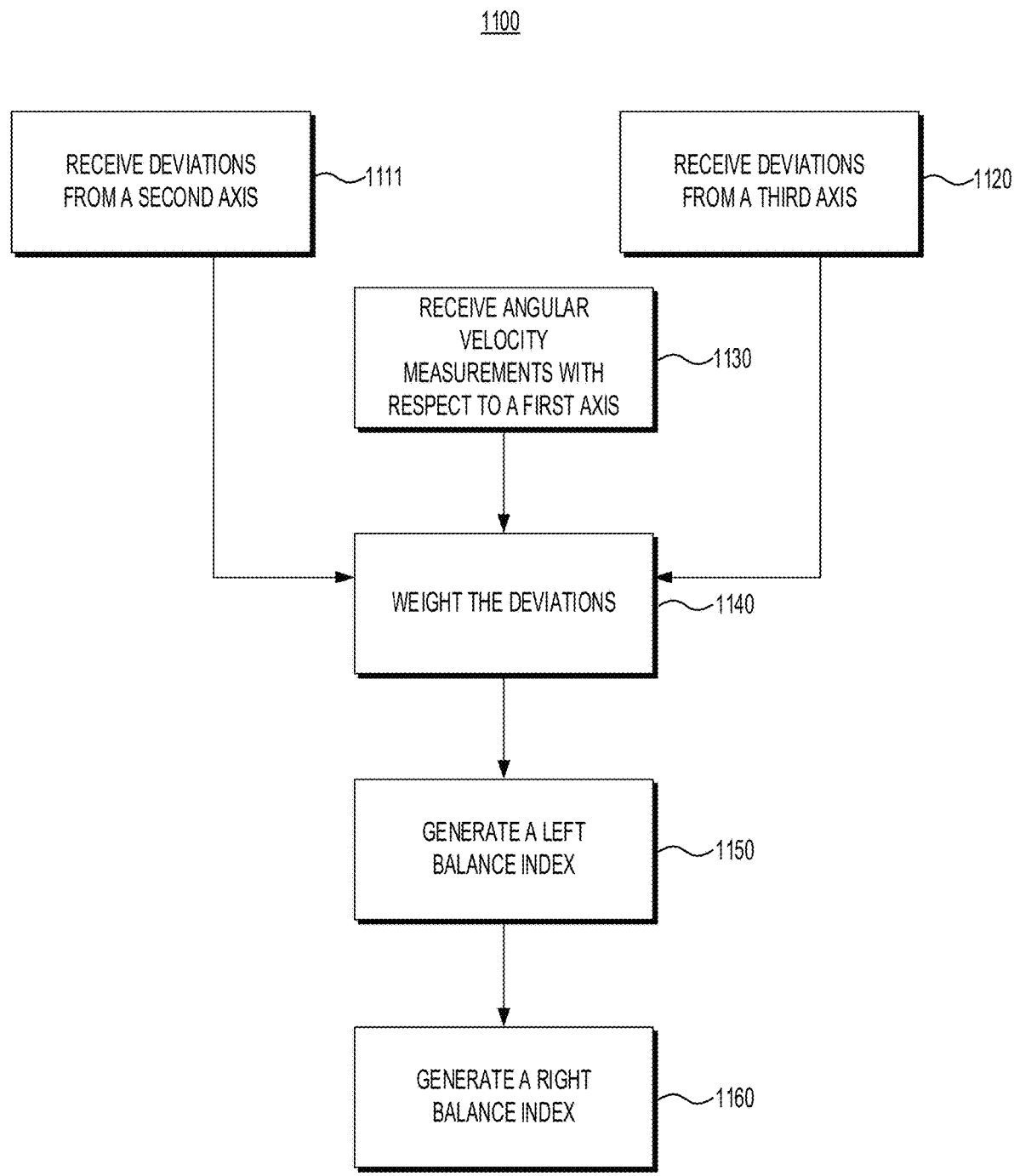
FIG. 11 is a flow diagram illustrating a process for generating left and right balance indices in accordance with some embodiments of the present disclosure.

FIG. 11 is a flow diagram illustrating a process for determining balance of a user in accordance with some embodiments of the present disclosure. Steps in the following discussion may be described with regard to the actions performed locally by sensor device 110. However, one or more alternative devices may instead perform the disclosed functions. For example, in an embodiment, computing device 120 may perform certain processing of environmental variables and/or selection of sampling rates locally (e.g., step 1040). Additionally, while the steps of process 1000 are shown in a particular order, the individual steps may be reordered or omitted.

Steps 1110, 1120, 1130, and 1140 may be performed similarly to steps 1010, 1020, 1030, and 1040, respectively, of process 1000 described above.

In step 1150, process 1100 may generate a left balance index based on the angular velocity measurements, the weighted deviations from the second axis, and the weighted deviations from the third axis. For example, sensor device 110 or computing device 120 may perform a weighted summation, a convolution, a multiplication, or any other combinatory resultant of angular velocities integrated over the period of time and the weighted deviations. To localize the balance index from step 1150 to a left side of the user, sensor device 110 or computing device 120 may separate deviations in a half-space corresponding to the left side of the user from deviations in a half-space corresponding to the right side of the user and only use the former in step 1150. Sensor device 110 or computing device 120 may separate the deviations before weighting or after weighting but before step 1150. Additionally or alternatively, sensor device 110 or computing device 120 may separate angular velocity measurements caused by movement in a half-space corresponding to the left side of the user from angular velocity measurements caused by movement in a half-space corresponding to the right side of the user and only use the former in step 1150.

In step 1160, process 1100 may generate a right balance index based on the angular velocity measurements, the weighted deviations from the second axis, and the weighted deviations from the third axis. For example, similar to step 1160, sensor device 110 or computing device 120 may perform a weighted summation, a convolution, a multiplication, or any other combinatory resultant of angular velocities integrated over the period of time and the weighted deviations. To localize the balance index from step 1160 to a left side of the user, sensor device 110 or computing device 120 may separate deviations in a half-space corresponding to the left side of the user from deviations in a half-space corresponding to the right side of the user and only use the latter in step 1160. Sensor device 110 or computing device 120 may separate the deviations before weighting or after weighting but before step 1160. Additionally or alternatively, sensor device 110 or computing device 120 may separate angular velocity measurements caused by movement in a half-space corresponding to the left side of the user from angular velocity measurements caused by movement in a half-space corresponding to the right side of the user and only use the latter in step 1160.

Accordingly, the index associated with the left side may be associated with a first half-space bounded by an axis of a body of the user, and the index associated with the right side may be associated with a second half-space bounded by the axis. The axis may comprise, e.g., the z-axis as depicted in FIG. 9, or any other axis dividing the body of the user into two half-spaces.

In some embodiments, balance scoring may be used in different contexts. In any of the embodiments below, raw balance scores may be used. For example, a raw balance score may comprise a balance score calculated directly from measurements of sensor device 110 and not adjusted, whether according to baseline or otherwise. Additionally or alternatively, balance scores relative to one or more baselines may be used. For example, baselines may include a period of time for balancing with eyes open, a period of time for balancing with eyes closed, a period of time for balancing with a right foot in front of a left foot and/or a left foot in front of a right food, a period of time for balancing with a left foot raised and/or a right foot raised, or any other position used to establish a baseline balance index.

Additionally or alternatively, balance scores relative to one or more goals may be used. For example, one or more balance goals may be set, e.g., based on historical balance scores associated with a user, by a physical therapist of the user, or any other manual or automatic technique for setting a goal. Accordingly, subsequent balance scores may be represented as percentages or any other indications of progress toward the one or more goals.

In such embodiments, the one or more goals may change according to a schedule. For example, the schedule may be determined using historical data from the user and/or historical data from similar users (e.g., indicated as having same diagnoses or one or more similar diagnoses or the like). Additionally or alternatively, a physical therapist for the user may input the schedule and/or adjust the schedule depending on the user's progress. Accordingly, subsequent balance scores may additionally or alternatively be displayed with reference to the schedule, e.g., whether a balance score of a particular day matches a goal of that day determined from the schedule, how close the balance score of a particular day matches the goal of that day determined from the schedule, or the like.

In accordance with embodiments disclosed herein, a 10-second balance test on one foot, for example, may result in angular velocity measurements from one or more IMUs of sensor device 110. After performing any smoothing algorithms or error correction algorithms, sensor device 110 or computing device 120 may determine deviations associated with each axis (e.g., as depicted in FIG. 9). Sensor device 110 or computing device 120 may determine the deviations using the angular velocity measurements from one or more gyroscopes. optionally fusing such measurements with measurements from one or more accelerometers and/or from a magnetometer. For example, sensor device 110 or computing device 120 may integrate the angular velocity measurements from one or more gyroscopes and apply one or more transforms to the integrated angular velocity measurements, optionally fusing the same with measurements from one or more accelerometers and/or from a magnetometer. For example, fusing may provide for calculations of deviations along orientation vectors (e.g., as depicted in FIG. 9) defined by the magnetometer and/or refined according to the one or more accelerometers. Accordingly, as shown in Example Table 2, deviations in the z-axis may represent deviations from a median (or any other statistical measure) angular velocity around the axis. This may represent an expected path of a user's head, for example, during normal balancing corrections. Moreover, as shown in Example Table 2, deviations in the x-axis and y-axis may represent absolute or directional deviations, respectively. This may represent, for example, an increased severity of backward deviations compared with forward deviations and/or an increased severity of lateral deviations compared with forward deviations. Using the determined deviations in this example, balance scores determined from corresponding weighting with corresponding calculations follows in Example Table 2 below, which is exemplary only and not exclusive:

TABLE 2

(exemplary only)

| Time (t) | z-deviations (with respect to median angular velocity around axis) | x-deviations (absolute value) | y-deviations (directional) |
| --- | --- | --- | --- |
| 1 s | 0.0 rad. | 0.2 rad. | +0.2 rad. |
| 2 s | 0.1 rad. | 0.3 rad. | +0.3 rad. |
| 3 s | 0.2 rad. | 0.1 rad. | −0.1 rad. |
| 4 s | 0.1 rad. | 0.3 rad. | −0.1 rad. |
| 5 s | 0.1 rad. | 0.4 rad. | +0.1 rad. |
| 6 s | 0.0 rad. | 0.1 rad. | 0.0 rad |
| 7 s | 0.1 rad. | 0.2 rad. | +0.1 rad. |
| 8 s | 0.3 rad. | 0.2 rad. | +0.4 rad. |
| 9 s | 0.3 rad. | 0.0 rad. | −0.5 rad. |
| 10 s | 0.0 rad | 0.0 rad. | −0.1 rad. |
| Score Components | Total of deviations = 0.12 rad. | Total of cubed deviations = 0.144 rad. | Total of squared positive deviations and fourth-power negative deviations = 0.3728 rad. |
| Final Score = 6.368 | | | |

Although Table 2 shows one measurement per second for simplicity, embodiments of the present disclosure may capture measurements at 50 Hz or greater. Moreover, although depicted as equal, some sensors (e.g., an accelerometer) may capture at a faster or slower rate than other sensors (e.g., a gyroscope). In such embodiments, sensor device 110 may normalize and/or downsample measurements from the faster sensor before calculating a balance score.

In one use case, embodiments of the present disclosure may be used to assess pre-op and post-op balance indices. Accordingly, pre-op assessments may indicate that a patient should strength one or more legs prior to a surgery on that leg or another leg. Moreover, post-op assessments may be used to track progress of strengthened a leg that was operated on and to ensure that strength in the other leg is not lost during physical therapy on the operated-on leg.

In another use case, embodiments of the present disclosure may be used to assess balance indices in elderly populations. For example, composite balance scores may indicate whether individuals are fall risks if below a clinical threshold. Moreover, left and right balance scores may indicate whether individuals draft feet when walking depending on which, if either, score is below a clinical threshold.

In yet another use case, embodiments of the present disclosure may be used to assess balance indices in sports players. For example, balance scores during competitions and practices may be compared to baselines to determine possible long-term effects of impact events. Accordingly, injuries to quarterbacks' legs, boxers' ears, or any other body parts related to balance may be detected and treated sooner and more effectively.

Similarly, embodiments of the present disclosure may be used to assess balance indices in physical careers. For example, balance scores during a workday may be compared to baselines to determine possible long-term effects of impact events. Accordingly, injuries to movers' backs, warehouse workers' legs, or any other body parts related to balance may be detected and treated sooner and more effectively.

In another use case, embodiments of the present disclosure may be used to assess balance indices to determine if installed floors are level. For example, balance scores on flooring surfaces may be compared to baselines to determine possible irregularities or slopes in the flooring surface.

In yet another use case, embodiments of the present disclosure may be used to assess balance indices in driving populations. For example, composite balance scores may indicate whether individuals are intoxicated if below a legal threshold. Moreover, composite, left, or right balance scores may indicate whether individuals are too incapacitated to safely operate a vehicle.

In another use case, embodiments of the present disclosure may be used to diagnose vertigo or any other conditions affecting balance. For example, balance scores may be compared to population baselines to detect possible diagnoses. Accordingly, some diagnoses may be detected and treated earlier than with existing methods.

The above use cases are exemplary only and not limiting of the embodiments disclosed herein.

Certain embodiments of this disclosure have been discussed with relation to a human skeletal system. However, the disclosed, calibration, kinematic data capture, and analysis techniques may be applied to any system with an expected or known baseline joint structure. In some embodiments, the disclosed methods may be applied to a sensor device (e.g., sensor device 110) mounted or attached to machine "skeletons" or structures (e.g., robotic equipment, computer numerical control (CNC) machine tools, robotically assisted surgery), animals (e.g., horses), partial human skeletons (e.g., amputees), and/or human skeletons with artificial limbs (e.g., prosthetics, orthotics). For each of these structural systems, a baseline map of possible or expected movements for each portion and/or the types of joints in them may be used to evaluate the movement of them using the previously discussed systems and methods. For example, one or more sensor devices may be attached to a horse (e.g., at the leg, head, and/or body), and disclosed systems and methods may determine an index for the horse, which may indicate whether the horse favors its front or rear legs and left or right legs.

It is intended that the disclosure and examples be considered as exemplary only, with a true scope and spirit of disclosed embodiments being indicated by the following claims.

What is claimed is:

1. A wearable device for determining balance of a user, comprising:
   at least one gyroscope configured to measure angular velocity about a first axis;
   at least one inertial measurement device configured to measure deviation along a second axis and a third axis;
   at least one memory storing instructions; and
   at least one processor configured to execute the instructions to perform operations, comprising:
      receiving angular velocity measurements over a period of time from the at least one gyroscope;
      receiving deviations from the second axis over the period of time from the at least one inertial measurement device;
      weighting the deviations from the second axis based on directions associated with the deviations;
      receiving deviations from the third axis over the period of time from the at least one inertial measurement device;
      weighting the deviations from the third axis based on directions associated with the deviations; and
      based on the angular velocity measurements, the weighted deviations from the second axis, and the weighted deviations from the third axis, determining an index associated with a left side of the user and an index associated with a right side of the user.

2. The device of claim 1, wherein the operations further comprise:
   normalizing the angular velocity measurements over the period of time; and
   normalizing the deviations from the second axis and the deviations from the third axis over the period of time before weighting.

3. The device of claim 1, wherein the weight for the second axis is greater for a first direction than a second, opposite direction.

4. The device of claim 3, wherein a deviation from the second axis in the first direction is squared, and a deviation in the second direction along the second axis has a power of four.

5. The device of claim 1, wherein the weight for the second axis is the same for a first direction and for a second, opposite direction.

6. The device of claim 5, wherein a deviation in the first direction and the second direction along the second axis is cubed.

7. The device of claim 1, wherein the weight for the third axis is greater for a first direction than a second, opposite direction.

8. The device of claim 1, wherein the weight for the third axis is the same for a first direction and for a second, opposite direction.

9. The device of claim 1, wherein the operations further comprise:
   weighting the angular velocity measurements based on a standard deviation from plumb over the period of time.

10. The device of claim 1, wherein the operations further comprise:
    outputting at least one of the index associated with the left side of the user or the index associated with the right side of the user to an external device associated with the user.

11. The device of claim 10, wherein outputting at least one of the index associated with the left side of the user or the index associated with the right side of the user comprises transmitting at least one of the index associated with the left side of the user or the index associated with the right side of the user over at least one wireless network.

12. The device of claim 1, wherein the operations further comprise:
    outputting a graphical depiction of the deviations from the second axis and the deviations from the third axis over the period of time to an external device associated with the user.

13. The device of claim 12, wherein outputting the graphical depiction of the deviations comprises transmitting the deviations over at least one wireless network.

14. The device of claim 1, wherein the operations further comprise:
    outputting the deviations from the second axis normalized over the period of time and the deviations from the third axis normalized over the period of time to an external device associated with the user.

15. The device of claim 14, wherein outputting the graphical depiction of the deviations comprises transmitting the deviations over at least one wireless network.

16. The device of claim 1, wherein the operations further comprise:
    determining a placement of the wearable device; and
    selecting weights based on the placement.

17. The device of claim 16, wherein the placement comprises at least one of placement on a head, placement on a hip, or placement on a neck.

18. The device of claim 17, wherein one or more weights associated with at least one of the second axis or the third axis are greater for the placement on the head or the placement on the neck than the placement on the hip.

19. The device of claim 1, wherein the index associated with the left side is associated with a first half-space bounded by an axis of a body of the user, and the index associated with the right side is associated with a second half-space bounded by the axis.

20. The device of claim 1, wherein the operations further comprise:
    generating a composite balance index based on the angular velocity measurements, the weighted deviations from the second axis, and the weighted deviations from the third axis.

* * * * *